(12) United States Patent
Simon et al.

(10) Patent No.: US 6,270,975 B1
(45) Date of Patent: Aug. 7, 2001

(54) GROUP O HIV-1, FRAGMENTS OF SUCH VIRUSES, AND USES THEREOF

(75) Inventors: François Simon, Paris; Sentob Saragosti, Boulogne-Billancourt; Ibtissam Loussert-Ajaka, Sartrouville; Thoai-Duong Ly, Rueil-Malmaison; Marie-Laure Chaix-Baudier, Paris, all of (FR)

(73) Assignees: Institut National de la Sante et de la Recherche Medicale-Inserm; Assistance Publique-Hopitaux de Paris, both of Paris (FR)

( * ) Notice: Subject to any disclaimer, the term of this patent is extended or adjusted under 35 U.S.C. 154(b) by 0 days.

(21) Appl. No.: 09/444,410
(22) Filed: Nov. 22, 1999

Related U.S. Application Data

(62) Division of application No. 08/894,699, filed on Dec. 1, 1997, now Pat. No. 6,030,769.

(30) Foreign Application Priority Data

Feb. 27, 1995 (FR) .................................. 95 02236

(51) Int. Cl.⁷ ............................ C12Q 1/68; C07H 21/02; C07H 21/04
(52) U.S. Cl. ............................ 435/6; 536/23.1; 536/24.3
(58) Field of Search ................................ 435/6; 536/23.1, 536/24.3

*Primary Examiner*—Hankyel T. Park
(74) *Attorney, Agent, or Firm*—Oblon, Spivak, McClelland, Maier & Neustadt, P.C.

(57) ABSTRACT

Group HIV-1 retrovirus strains, particularly the strains known as BCF02, BCF01, BCF06, BCF07, BCF08, BCF11, BCF03, BCF09, BCF12, BCF13 and BCF14, fragments of said retroviruses, and the uses thereof as a diagnostic reagent and as an immunogen, are disclosed.

8 Claims, 6 Drawing Sheets

FIG.1

```
                              gag CAp24

CONS    aISPRTLNAWVKAVEEKAFNPEIIPMFMALSEGAipYDINTMLNAIGgHQGALQVLKEVINeEAaeWDR

ANT70   .I..........................S...................................V....
MVP5180 .I.........................V.........................................

ESS     PI........................V............E.....................L.......
FAN     .I...........................................................D...D...
LOB     ..........................V...........................................
MAN     ................I..........V.S.........................................
NAN     ...........................V...........................D.............
NKO     .P......................................................D.............
PDC     .P......................................................SD...........

CONS    THppp*GPLPPGQIRePTGSDIAGTTSTQQEQvhW*TRpnnpiPVGDIYrKWIVIGLNKmVKmY

ANT70   .....V.................................T...Q.........................
MVP5180 ...AM.................................II.T.GA.S........................

ESS     ....I............D........................V.NP........W...F...L.......
FAN     ..T.V....................................I.........................L..
LOB     ..AM.............D........................IN.I.....V..................
MAN     ..I.V.............D........................T..........................
NAN     ....V......................................I.I..GG.S..................
NKO     ....I......................................I.I..A.QS..................
PDC     ....I.......................................T...Q.....................
```

FIG. 2

C2V3 Group O

FIG.3

GAG Groupe O

FIG.4

POC
NKO
NAN
MAN
LOB
FAN
ESS

872  MARQUEURS
1078  Φx174
1353
603  310-281-271

C2V3 Group 0

FIG.5

SEQUENCE LISTING (1) GENERAL INFORMATION:

(iii) NUMBER OF SEQUENCES: 81

(2) INFORMATION FOR SEQ ID NO:1:

(i) SEQUENCE CHARACTERISTICS:
      (A) LENGTH: 291 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

```
GTGGTTACTT GTACACATGG CATCAAGCCA ACAGTAAGTA CTCAGCTAAT ATTAAATGGA      60

ACACTCTCAG AAGGAAAGAT AAGAATGATG GCAAAAAATA TTTCGGATAG TGGCCAAAAT     120

ATCATAGTGA CCCTAAATAC TACTATAAAC ATGACCTGCC AGAGACCAGG ACATCAAACA     180

GTACAAGAGA TAAGGATAGG TCCAATGGCC TGGTACAGCA TGGGCTTAGC GGCAGGAAAC     240

GGATCTGAGT CAAGAAGAGC TTATTGTGAA TATAATACCA CTAATTGGAT A             291
```

(2) INFORMATION FOR SEQ ID NO:2:

(i) SEQUENCE CHARACTERISTICS:
      (A) LENGTH: 294 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:2:

```
GTAGTTACTT GTACACATGG CATCAAGCCA ACAGTGAGTA CTCATCTAAT ATTAAATGGG      60

ACAATCTCTG AAGGAGAAAT AAGAATTATG GGAAAAAATA TTCGGGAAAA TGCTAAAAAT     120

ATCATAGTGA CCCTAAATTC TACTATAAAC ATGACCTGTG AGAGACCAGA GGGAAATCTG     180

ACAATACAAG AGATACACTC AGGACCAATG GCCTGGTACA GCTTGGGACT AAAGAGAAAT     240

ACAACCGTAA GATCAAGATC AGCTCATTGC AAGTATAACA CCACTAATTG GAA           294
```

-continued (2) INFORMATION FOR SEQ ID NO:3:

(i) SEQUENCE CHARACTERISTICS:
        (A) LENGTH: 297 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

```
GTGGTTACTT GTACACATGG CATCAAGCCA GCAGTAAGTA CTCAGCTAAT ATTAAATGGG    60

ACACTCTCTA AAGGAAAAAT AAGAATTATG GCAAAAAATA TTACAAACAC TGGGAATAAT   120

ATCATAGTGA CTCTAAATTC CACCATAAAC ATAACCTGTA ACAGACCAGG AAGGGGAATA   180

AAACAGATAG GTATAGGTCC AATGTCCGTA TACAGCGGGA GCTTAGCGGA CTTAGGGGA    240

AACAACAACT CAAGGATAGC TTATTGCGAT TATGACATCA CTAAGTGGAA CGAAACA      297
```

(2) INFORMATION FOR SEQ ID NO:4:

(i) SEQUENCE CHARACTERISTICS:
        (A) LENGTH: 294 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

```
GTAGTTACTT GTACACATGG CATCAAGCCA ACAGTAAGTA CTCAATTAAT AATGAATGGG    60

ACACTCTCTA GAGGGAAGAT AAGAATTATG GGAAGAAATA TTACAGACAA TACAAAGAAT   120

ATTATAGTAA CCTTAAACAC TTCTATAAAC ATGACATGTA TGAGAAAAGG AAGAGGTAAA   180

ATACAAAGGA TAGCGACAGG TCCACTGCGA TGGGTCAGTA TGGCAGCTAA AACAGAGTCA   240

CAGAACACAG GGTCAAGGAT AGCTTATTGT ATGTATAATA ACACTGAATG GATA         294
```

(2) INFORMATION FOR SEQ ID NO:5:

(i) SEQUENCE CHARACTERISTICS:
        (A) LENGTH: 291 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

```
GTGGTTACTT GTACACATGG CATCAAGCCA ACAGTAAGTA CTCAGCTAAT ATTAAATGGA    60

ACACTCTCGA AAGGAAAGAT AAGACTGATG GCAAAAAATA TTTCGGATAG TGGCCAAAAT   120

ATCATAGTGA CCCTAAATAC TACTATAAAC ATGACCTGCC ATAGACCAGG AAATCTAAAA   180

GTACAGGAGA TAAAGATAGG TCCAATGGCC TGGTACAGCA TGGGCATAGA GAATGAAAAC   240

ATACCTGATT CAAGAAAAGC TTATTGTGAT TATAATACCA CTAAGTGGGT A            291
```

(2) INFORMATION FOR SEQ ID NO:6:

(i) SEQUENCE CHARACTERISTICS:
        (A) LENGTH: 291 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

GTAGTTACTT GTACACATGG CATCAAGCCC ACAGTGAGTA CTCAACTGAT ATTAAATGGG      60

ACACTCTCTG AAAAGGGAAT AAGAATTATG GGAAAAAACA TTTCAAAAAC TGGGGAAAAT     120

ATCATAGTGA CCCTAAATGT AAGCATAAAC ATTACTTGTC ATAGACCAGG AAATCTGTCA     180

GTACAAGAGA TGAAAATAGG TCCACTGTCC TGGTACAGCA TGGGCCTAGC GGCAAACTCA     240

AGCATAAAGT CAAGGGTAGC TTATTGCAAT TATAGTACCA CTGAATGGAC A              291

(2) INFORMATION FOR SEQ ID NO:7:

(i) SEQUENCE CHARACTERISTICS:
        (A) LENGTH: 296 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

GTGGTTACTT GACACATGGC ATCAAGCCAG CAGTAAGTAC TCAACTAATA CTAAATGGGA      60

CACTCTCTGA AGGGAAGATA AGAATTATGG GACAAAATAT CTCTGACAGT GGAAAGAATA     120

TCATAGTAAC CCTAAATAAG ACTGTAAACA TGAACATAAC CTGCACAAGA GATGGAGATC     180

AGAAGGTACA AGAGATAGGG ATAGGTCCAC TGTCATGGTA CAGTATGAGC ATTGCAGAAG     240

ACAGCGCTAA AAACACAAGA GCAGCTTATT GTAACTATAG TGCAAGTAGT TGGAAG         296

(2) INFORMATION FOR SEQ ID NO:8:

(i) SEQUENCE CHARACTERISTICS:
        (A) LENGTH: 120 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

AGACAACTCC GAGCTCGCCT GCTAGCCTTA GAAACCTTAA TACAGAATCA GCAACTCCTA      60

AACTCGTGGG GCTGTAAGGG AAGGATAGTC TGCTACACAT CAGTAAAATG GAACTGGACA     120

(2) INFORMATION FOR SEQ ID NO:9:

(i) SEQUENCE CHARACTERISTICS:
        (A) LENGTH: 120 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

AGACAACTCC GAGCTCGCCT GCTAGCCTTA GAAACCTTAA TACAGAATCA GCAACTCCTA      60

AACCTATGGG GCTGTAAGGG AAGGCTACTC TGCTACACAT CAGTAAAATG GAATACGACA     120

(2) INFORMATION FOR SEQ ID NO:10:

(i) SEQUENCE CHARACTERISTICS:
        (A) LENGTH: 120 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

AGACAACTCC GAGCTCGCCT GCAAGCCTTA GAAACCTTAA TCCAGAATCA GCAACTCCTA        60

AGCCTGTGGG GCTGTAAAGG AAGGCTAGTC TGCTACACAT CAGTAAAATG GCACAACACA       120

(2) INFORMATION FOR SEQ ID NO:11:

(i) SEQUENCE CHARACTERISTICS:
        (A) LENGTH: 120 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

AGACAACTCC GAGCTCGCCT GCAAGCCTTA GAACCCCTTA TACAGAATCA GCAACGCCTA        60

AGCCTATGGG GATGTAAGGG AAGGATAATA TGTTACACAT CAGCAAAATG GAACAACACA       120

(2) INFORMATION FOR SEQ ID NO:12:

(i) SEQUENCE CHARACTERISTICS:
        (A) LENGTH: 120 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

AGACAACTCC GAGCTCGCCT GCTAGCCTTA GAAACCTTAA TACAGAATCA GCAACTCCTA        60

AACTCATGGG GCTGTAAGGG AAGGCTAGTC TGTTACACAT CAGTAAAATG GAACGAGACA       120

(2) INFORMATION FOR SEQ ID NO:13:

(i) SEQUENCE CHARACTERISTICS:
        (A) LENGTH: 120 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

AGACAACTCC GAGCTCGCCT GCTAGCCTTA GAAACCTTGA TACAGAATCA GCAACTCCTA        60

AACCTATGGG GCTGTAAGGG AAGGCTACTC TGCTACACAT CAGTAAAATG GAACAGTACA       120

(2) INFORMATION FOR SEQ ID NO:14:

(i) SEQUENCE CHARACTERISTICS:
        (A) LENGTH: 120 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

AGACAACTCC GAGCTCGCCT GGTTGCCTTA GAAACCTTG TACAGAATCA GCAACTCCTA         60

AACCTATGGG GCTGTAAAGG AAGACTAACA TGCTATACAT CAGTAAAATG GAATGACACA       120

(2) INFORMATION FOR SEQ ID NO:15:

(i) SEQUENCE CHARACTERISTICS:

(A) LENGTH: 399 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

CCCATTTCTC CTAGAACTTT AAATGCATGG GTAAAGGCAG TAGAAGAGAA AGCCTTTAAC      60

CCTGAAATCA TTCCTATGTT CATGGCATTG TCAGAGGGAG CTGTTCCCTA TGATATTAAT     120

ACTATGCTAA ATGCCATAGG AGAACATCAA GGGGCTTTAC AAGTGCTAAA GGAAGTAATC     180

AATGAGGAAG CATTGGAGTG GGATAGAACT CACCCACCAC CGATAGGGCC GTTACCACCA     240

GGGCAGATAA GGGACCCAAC AGGAAGTGAC ATTGCTGGAA CAACTAGCAC TCAGCAAGAG     300

CAAGTTCACT GGGTGACCAG GAACCCCAAC CCTATCCCAG TAGGAGACAT CTATTGGAAA     360

TGGATAGTGT TTGGGCTTAA CAAATTGGTT AAAATGTAC                            399

(2) INFORMATION FOR SEQ ID NO:16:

(i) SEQUENCE CHARACTERISTICS:
        (A) LENGTH: 399 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

CCCCTCTCCC CCAGGACTTT AAATGCATGG GTAAAGGCAG TAGAAGAAAA AGCCTTTAAC      60

CCTGAGATCA TTCCTATGTT CATGGCATTG TCAGAGGGAG CTATTCCCTA TGATATTAAT     120

ACTATGCTAA ATGCCATAGG AGGACATCAA GGAGCCCTAC AAGTGCTAAA GGAAGTAATC     180

AATGAGGAAG CAGCAGATTG GGATAGAACT CACCCGCCAC CGATAGGGCC ATTACCACCA     240

GGGCAGATAA GGGAACCAAC AGGAAGTGAC ATTGCTGGGA CAACTAGCAC CCAGCAAGAG     300

CAAGTTCACT GGATTACCAG AGCCAACCAA TCTATCCCAG TAGGAGACAT CTATAGAAAA     360

TGGATAGTGT TAGGACTAAA CAAAATGGTA AAAATGTAC                            399

(2) INFORMATION FOR SEQ ID NO:17:

(i) SEQUENCE CHARACTERISTICS:
        (A) LENGTH: 399 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

CCCCTCTCCC CCAGGACTCT AAATGCATGG GTAAAGGCAG TAGAAGAAAA AGCCTTTAAC      60

CCTGAAATCA TTCCTATGTT CATGGCATTG TCAGAGGGAG CAATTCCCTA TGATATTAAT     120

ACTATGCTAA ATGCCATAGG AGGACATCAA GGAGCTTTAC AAGTGTTAAA GGAAGTAATC     180

AATGAGGAAG CATCAGATTG GGATAGAACT CACCCACCAC CGATAGGGCC GCTGCCTCCA     240

GGGCAAATAA GGGAACCAAC AGGAAGTGAC ATTGCTGGGA CAACTAGTAC CCAGCAAGAG     300

CAAGTTCACT GGACTACCAG ACCCAATCAA CCTATCCCAG TAGGAGACAT CTATAGAAAA     360

TGGATAGTGT TAGGACTAAA CAAAATGGTA AAAATGTAC                            399

(2) INFORMATION FOR SEQ ID NO:18:

(i) SEQUENCE CHARACTERISTICS:
  (A) LENGTH: 399 base pairs
  (B) TYPE: nucleic acid
  (C) STRANDEDNESS: single
  (D) TOPOLOGY: linear (ii) MOLECULE TYPE: DNA (genomic)

(xi) SEQUENCE DESCRIPTION: SEQ ID NO:18:

| | | | | | | |
|---|---|---|---|---|---|---|
| GCCCTCTCCC | CCAGGACGTT | AAATGCATGG | GTAAAGGCAG | TAGAAGAAAA | GGCCTTTAAC | 60 |
| CCTGAAATTA | TTCCTATGTT | TATGGCATTA | TCAGAAGGAG | CTGTTCCCTA | TGATATCAAT | 120 |
| ACCATGCTAA | ATGCCATAGG | AGGACACCAA | GGGGCTTTAC | AAGTGTTGAA | GGAAGTAATC | 180 |
| AATGAGGAAG | CAGCAGAATG | GGATAGAACT | CATCCACCAG | CAATGGGGCC | GTTACCACCA | 240 |
| GGGCAGCTAA | GAGATCCAAC | AGGAAGTGAC | ATTGCTGGAA | CAACTAGCAC | ACAGCAAGAG | 300 |
| CAAATTAACT | GGATTACTAG | ACCAAATAAC | CCTGTCCCTG | TAGGAGACAT | CTATAGAAAA | 360 |
| TGGATAGTGC | TAGGATTAAA | TAAAATGGTA | AAGTTGTAC | | | 399 |

(2) INFORMATION FOR SEQ ID NO:19:

(i) SEQUENCE CHARACTERISTICS:
    (A) LENGTH: 399 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:19:

| | | | | | | |
|---|---|---|---|---|---|---|
| GCCCTTTCCC | CTAGAACTTT | AAATGCATGG | GTAAAGGCAG | TAGAAGAAAA | AGCCTTTAAC | 60 |
| CCTGAAATCA | TTCCTATGTT | CATGGCATTG | TCAGAGGGAG | CTATTTCCTA | TGACATTAAT | 120 |
| ACTATGCTAA | ATGCCATAGG | AGGACATCAA | GGGGCTTTAC | AAGTGCTAAA | GGAAGTAATC | 180 |
| AATGAGGAAG | CAGCAGAGTG | GGATAGAACT | CACCCAATAC | CGGTAGGGCC | GTTACCACCA | 240 |
| GGGCAGATAA | GGGACCCAAC | AGGAAGTGAC | ATTGCTGGGA | CAACTAGCAC | CCAGCAAGAA | 300 |
| CAAGTTCACT | GGACAACCAG | ACCCAACAAC | CCTATCCCAG | TAGGAGACAT | CTATAGGAAA | 360 |
| TGGATAGTGT | TGGGGCTTAA | CAAAATGGTA | AAAATGTAC | | | 399 |

(2) INFORMATION FOR SEQ ID NO:20:

(i) SEQUENCE CHARACTERISTICS:
    (A) LENGTH: 399 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:20:

| | | | | | | |
|---|---|---|---|---|---|---|
| GCTATCTCCC | CCAGGACTTT | AAATGCATGG | GTAAAGGCAG | TAGAAGAGAA | GGCCTTTAAC | 60 |
| CCTGAAATCA | TTCCTATGTT | CATGGCATTG | TCAGAGGGAG | CTATTCCCTA | CGATATTAAT | 120 |
| ACCATGCTAA | ATGCCATAGG | AGGACATCAA | GGAGCCTTGC | AGGTGCTAAA | GGAAGTAATC | 180 |
| AATGATGAAG | CAGCAGATTG | GGATAGAACT | CACACACCAG | CGGTAGGGCC | GTTGCCACCA | 240 |
| GGGCAGATAA | GGGAACCAAC | AGGAAGTGAC | ATTGCTGGGA | CAACTAGCAC | CCAGCAAGAG | 300 |
| CAAGTTCATT | GGATTACTAG | GCCCAACAAC | CCTATCCCAG | TAGGAGACAT | CTATAGAAAA | 360 |
| TGGATAGTGT | TAGGGTTAAA | CAAAATGGTA | AAAATGTAC | | | 399 |

(2) INFORMATION FOR SEQ ID NO:21:

(i) SEQUENCE CHARACTERISTICS:
        (A) LENGTH: 399 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:21:

```
GCCCTCTCCC CCAGGACTTT AAATGCATGG GTAATAGCAG TAGAAGAGAA AGCCTTTAAC      60
CCTGAAATTA TTCCTATGTT TATGGCATTA TCAGAAGGAG CTGTTCCCTA TGATATCAAT     120
ACCATGCTAA ATGCCATAGG AGGACACCAG GGGGCTTTAC AAGTGTTGAA GGAAGTGATC     180
AATGAAGAAG CAGCAGATTG GGACAGAACT CATCCACCAC CAGTAGGGCC GTTACCACCA     240
GGTCAGATAA GGGAACCAAC AGGGAGTGAT ATTGCTGGAA CCACTAGCAC ACAGCAAGAG     300
CAAATTCACT GGATTACTAG GGGAGGTAAT TCTATCCCAG TAGGAGACAT ATATAGGAAA     360
TGGATAGTGC TAGGATTAAA CAAAATGGTA AAAATGTAC                            399
```

(2) INFORMATION FOR SEQ ID NO:22:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(xi) SEQUENCE DESCRIPTION: SEQ ID NO:22:

```
AGRGAAAAAA GAGCAGTAGG AT                                               22
```

(2) INFORMATION FOR SEQ ID NO:23:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(xi) SEQUENCE DESCRIPTION: SEQ ID NO:23:

```
TCTAAGTGCA GCAGGTAGCA CTAT                                             24
```

(2) INFORMATION FOR SEQ ID NO:24:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(xi) SEQUENCE DESCRIPTION: SEQ ID NO:24:

```
CTAAGTTGCT CAAGAGTGGT A                                                21
```

(2) INFORMATION FOR SEQ ID NO:25:

(i) SEQUENCE CHARACTERISTICS:

(A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(xi) SEQUENCE DESCRIPTION: SEQ ID NO:25:

GTTGCTCAAG AGGTGGTAAG T                                      21

(2) INFORMATION FOR SEQ ID NO:26:

(i) SEQUENCE CHARACTERISTICS:
        (A) LENGTH: 97 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:26:

Val Val Thr Cys Thr His Gly Ile Lys Pro Thr Val Ser Thr Gln Leu
1               5                   10                  15

Ile Leu Asn Gly Thr Leu Ser Glu Gly Lys Ile Arg Met Met Ala Lys
            20                  25                  30

Asn Ile Ser Asp Ser Gly Gln Asn Ile Ile Val Thr Leu Asn Thr Thr
        35                  40                  45

Ile Asn Met Thr Cys Gln Arg Pro Gly His Thr Val Gln Glu Ile
    50                  55                  60

Arg Ile Gly Pro Met Ala Trp Tyr Ser Met Gly Leu Ala Asn Gly Asn
65                  70                  75                  80

Gly Ser Glu Ser Arg Arg Ala Tyr Cys Glu Tyr Asn Thr Thr Asn Trp
                85                  90                  95

Ile (2) INFORMATION FOR SEQ ID NO:27:

(i) SEQUENCE CHARACTERISTICS:
        (A) LENGTH: 97 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:27:

Val Val Thr Cys Thr His Gly Ile Lys Pro Thr Val Ser Thr Gln Leu
1               5                   10                  15

Ile Leu Asn Gly Thr Leu Ser Glu Lys Gly Ile Arg Ile Met Gly Lys
            20                  25                  30

Asn Ile Ser Lys Thr Gly Glu Asn Ile Ile Val Thr Leu Asn Val Ser
        35                  40                  45

Ile Asn Ile Thr Cys His Arg Pro Gly Asn Leu Ser Val Gln Glu Met
    50                  55                  60

Lys Ile Gly Pro Leu Ser Trp Tyr Ser Met Gly Leu Ala Ala Asn Ser
65                  70                  75                  80

Ser Ile Lys Ser Arg Val Ala Tyr Cys Asn Tyr Ser Thr Thr Glu Trp
                85                  90                  95

Thr (2) INFORMATION FOR SEQ ID NO:28:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:28:

Arg Ser Val Gln Glu Met Lys Ile Gly Pro Leu Ser Trp Tyr Ser Met
1               5                   10                  15

Gly Leu Ala Ala Asn Ser Ser Ile Lys
            20                  25

(2) INFORMATION FOR SEQ ID NO:29:

(i) SEQUENCE CHARACTERISTICS:
        (A) LENGTH: 98 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:29:

Val Val Thr Cys Thr His Gly Ile Lys Pro Thr Val Ser Thr Gln Leu
1               5                   10                  15

Ile Met Asn Gly Thr Leu Ser Arg Gly Lys Ile Arg Ile Met Gly Arg
            20                  25                  30

Asn Ile Thr Asp Asn Thr Lys Asn Ile Ile Val Thr Leu Asn Thr Ser
            35                  40                  45

Ile Asn Met Thr Cys Met Arg Lys Gly Arg Gly Lys Ile Gln Arg Ile
50                  55                  60

Ala Thr Gly Pro Leu Arg Trp Val Ser Met Ala Ala Lys Thr Glu Ser
65                  70                  75                  80

Gln Asn Thr Gly Ser Arg Ile Ala Tyr Cys Met Tyr Asn Asn Thr Glu
                85                  90                  95

Trp Ile (2) INFORMATION FOR SEQ ID NO:30:

(i) SEQUENCE CHARACTERISTICS:
        (A) LENGTH: 97 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:30:

Val Val Thr Cys Thr His Gly Ile Lys Pro Thr Val Ser Thr Gln Leu
1               5                   10                  15

Ile Leu Asn Gly Thr Leu Ser Lys Gly Lys Ile Arg Leu Met Ala Lys
            20                  25                  30

Asn Ile Ser Asp Ser Gly Gln Asn Ile Ile Val Thr Leu Asn Thr Thr
            35                  40                  45

Ile Asn Met Thr Cys His Arg Pro Gly Asn Leu Lys Val Gln Glu Ile
50                  55                  60

Lys Ile Gly Pro Met Ala Trp Tyr Ser Met Gly Ile Glu Ala Glu Asn
65                  70                  75                  80

Ile Pro Asp Ser Arg Lys Ala Tyr Cys Asp Tyr Asn Ala Thr Lys Trp
                    85                  90                  95
Val (2) INFORMATION FOR SEQ ID NO:31:

(i) SEQUENCE CHARACTERISTICS:
        (A) LENGTH: 99 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:31:

Val Val Thr Cys Thr His Gly Ile Lys Pro Ala Val Ser Thr Gln Leu
1               5                   10                  15

Ile Leu Asn Gly Thr Leu Ser Glu Gly Lys Ile Arg Ile Met Gly Gln
                20                  25                  30

Asn Ile Ser Asp Ser Gly Lys Asn Ile Ile Val Thr Leu Asn Lys Thr
                35                  40                  45

Val Asn Met Asn Ile Thr Cys Thr Arg Asp Gly Asp Gln Lys Val Gln
        50                  55                  60

Glu Ile Gly Ile Gly Pro Leu Ser Trp Tyr Ser Met Ser Ile Ala Glu
65                  70                  75                  80

Asp Ser Ala Lys Asn Thr Arg Ala Ala Tyr Cys Asn Tyr Ser Ala Ser
                85                  90                  95

Ser Trp Lys (2) INFORMATION FOR SEQ ID NO:32:

(i) SEQUENCE CHARACTERISTICS:
        (A) LENGTH: 98 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:32:

Val Val Thr Cys Thr His Gly Ile Lys Pro Thr Val Ser Thr His Leu
1               5                   10                  15

Ile Leu Asn Gly Thr Ile Ser Glu Gly Glu Ile Arg Ile Met Gly Lys
                20                  25                  30

Asn Ile Arg Glu Asn Ala Lys Asn Ile Ile Val Thr Leu Asn Ser Thr
                35                  40                  45

Ile Asn Met Thr Cys Glu Arg Pro Glu Gly Asn Leu Thr Ile Gln Glu
        50                  55                  60

Ile His Ser Gly Pro Met Ala Trp Tyr Ser Leu Gly Leu Lys Arg Asn
65                  70                  75                  80

Thr Thr Val Arg Ser Arg Ser Ala His Cys Lys Tyr Asn Thr Thr Asn
                85                  90                  95

Trp Glu (2) INFORMATION FOR SEQ ID NO:33:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:33:

Arg Thr Ile Gln Glu Ile His Ser Gly Pro Met Ala Trp Tyr Ser Leu
1               5                   10                  15

Gly Leu Lys Arg Asn Thr Thr Val Arg
            20                  25

(2) INFORMATION FOR SEQ ID NO:34:

(i) SEQUENCE CHARACTERISTICS:
         (A) LENGTH: 99 amino acids
         (B) TYPE: amino acid
         (C) STRANDEDNESS: single
         (D) TOPOLOGY: linear (ii) MOLECULE TYPE: protein (xi) SEQUENCE DESCRIPTION: SEQ ID NO:34:

Val Val Thr Cys Thr His Gly Ile Lys Pro Ala Val Ser Thr Gln Leu
1               5                   10                  15

Ile Leu Asn Gly Thr Leu Ser Lys Gly Lys Ile Arg Ile Met Ala Lys
                20                  25                  30

Asn Ile Thr Asn Thr Gly Asn Asn Ile Ile Val Thr Leu Asn Ser Thr
                35                  40                  45

Ile Asn Ile Thr Cys Asn Arg Pro Gly Arg Gly Ile Lys Gln Ile Gly
            50                  55                  60

Ile Gly Pro Met Ser Val Tyr Ser Gly Ser Leu Ala Asp Leu Gly Gly
65                  70                  75                  80

Asn Asn Asn Ser Arg Ile Ala Tyr Cys Asp Tyr Asp Ile Thr Lys Trp
                85                  90                  95

Asn Glu Thr (2) INFORMATION FOR SEQ ID NO:35:

(i) SEQUENCE CHARACTERISTICS:
         (A) LENGTH: 24 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:35:

Arg Ile Lys Gln Ile Gly Ile Gly Pro Met Ser Val Tyr Ser Gly Ser
1               5                   10                  15

Leu Ala Asp Leu Gly Asn Asn Asn
            20

(2) INFORMATION FOR SEQ ID NO:36:

(i) SEQUENCE CHARACTERISTICS:
         (A) LENGTH: 40 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:36:

Arg Gln Leu Arg Ala Arg Leu Leu Ala Leu Glu Thr Leu Ile Gln Asn
1               5                   10                  15

Gln Gln Leu Leu Asn Ser Trp Gly Cys Lys Gly Arg Ile Val Cys Tyr
            20                  25                  30

Thr Ser Val Lys Trp Asn Trp Thr
            35                  40

(2) INFORMATION FOR SEQ ID NO:37:

(i) SEQUENCE CHARACTERISTICS:
        (A) LENGTH: 40 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:37:

Arg Gln Leu Arg Ala Arg Leu Leu Ala Leu Glu Thr Leu Ile Gln Asn
1               5                   10                  15

Gln Gln Leu Leu Asn Leu Trp Gly Cys Lys Gly Arg Leu Leu Cys Tyr
            20                  25                  30

Thr Ser Val Lys Trp Asn Ser Thr
            35                  40

(2) INFORMATION FOR SEQ ID NO:38:

(i) SEQUENCE CHARACTERISTICS:
        (A) LENGTH: 40 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:38:

Arg Gln Leu Arg Ala Arg Leu Gln Ala Leu Glu Pro Leu Ile Gln Asn
1               5                   10                  15

Gln Gln Arg Leu Ser Leu Trp Gly Cys Lys Gly Arg Ile Ile Cys Tyr
            20                  25                  30

Thr Ser Ala Lys Trp Asn Asn Thr
            35                  40

(2) INFORMATION FOR SEQ ID NO:39:

(i) SEQUENCE CHARACTERISTICS:
        (A) LENGTH: 40 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:39:

Arg Gln Leu Arg Ala Arg Leu Leu Ala Leu Glu Thr Leu Ile Gln Asn
1               5                   10                  15

Gln Gln Leu Leu Asn Ser Trp Gly Cys Lys Gly Arg Leu Val Cys Tyr
            20                  25                  30

Thr Ser Val Lys Trp Asn Glu Thr
            35                  40

(2) INFORMATION FOR SEQ ID NO:40:

(i) SEQUENCE CHARACTERISTICS:
        (A) LENGTH: 40 amino acids
        (B) TYPE: amino acid
        (C) STRANDEDNESS: single (D) TOPOLOGY: linear (ii) MOLECULE TYPE: peptide (xi) SEQUENCE DESCRIPTION: SEQ ID NO:40:

Arg Gln Leu Arg Ala Arg Leu Leu Ala Leu Glu Thr Leu Ile Gln Asn
1               5                  10                  15

Gln Gln Leu Leu Asn Leu Trp Gly Cys Lys Gly Arg Leu Leu Cys Tyr
            20                  25                  30

Thr Ser Val Lys Trp Asn Thr Thr
        35                  40

(2) INFORMATION FOR SEQ ID NO:41:

(i) SEQUENCE CHARACTERISTICS:
            (A) LENGTH: 40 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:41:

Arg Gln Leu Arg Ala Arg Leu Gln Ala Leu Glu Thr Leu Ile Gln Asn
1               5                  10                  15

Gln Gln Leu Leu Ser Leu Trp Gly Cys Lys Gly Arg Leu Val Cys Tyr
            20                  25                  30

Thr Ser Val Lys Trp His Asn Thr
        35                  40

(2) INFORMATION FOR SEQ ID NO:42:

(i) SEQUENCE CHARACTERISTICS:
            (A) LENGTH: 40 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:42:

Arg Gln Leu Arg Ala Arg Leu Val Ala Leu Glu Thr Leu Val Gln Asn
1               5                  10                  15

Gln Gln Leu Leu Asn Leu Trp Gly Cys Lys Gly Arg Leu Thr Cys Tyr
            20                  25                  30

Thr Ser Val Lys Trp Asn Asp Thr
        35                  40

(2) INFORMATION FOR SEQ ID NO:43:

(i) SEQUENCE CHARACTERISTICS:
            (A) LENGTH: 133 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:43:

Pro Ile Ser Pro Arg Thr Leu Asn Ala Trp Val Lys Ala Val Glu Glu
1               5                  10                  15

Lys Ala Phe Asn Pro Glu Ile Ile Pro Met Phe Met Ala Leu Ser Glu
            20                  25                  30

Gly Ala Val Pro Tyr Asp Ile Asn Thr Met Leu Asn Ala Ile Gly Glu

```
                    35                  40                  45
His Gln Gly Ala Leu Gln Val Leu Lys Glu Val Ile Asn Glu Glu Ala
    50                  55                  60

Leu Glu Trp Asp Arg Thr His Pro Pro Ile Gly Pro Leu Pro Pro
 65                  70                  75                  80

Gly Gln Ile Arg Asp Pro Thr Gly Ser Asp Ile Ala Gly Thr Thr Ser
                85                  90                  95

Thr Gln Gln Glu Gln Val His Trp Val Thr Arg Asn Pro Asn Pro Ile
                100                 105                 110

Pro Val Gly Asp Ile Tyr Trp Lys Trp Ile Val Phe Gly Leu Asn Lys
                115                 120                 125

Leu Val Lys Met Tyr
        130
```

(2) INFORMATION FOR SEQ ID NO:44:

(i) SEQUENCE CHARACTERISTICS:
        (A) LENGTH: 133 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:44:

```
Ala Ile Ser Pro Arg Thr Leu Asn Ala Trp Val Lys Ala Val Glu Glu
 1               5                  10                  15

Lys Ala Phe Asn Pro Glu Ile Ile Pro Met Phe Met Ala Leu Ser Glu
                20                  25                  30

Gly Ala Ile Pro Tyr Asp Ile Asn Thr Met Leu Asn Ala Ile Gly Gly
                35                  40                  45

His Gln Gly Ala Leu Gln Val Leu Lys Glu Val Ile Asn Asp Glu Ala
    50                  55                  60

Ala Asp Trp Asp Arg Thr His Thr Pro Pro Val Gly Pro Leu Pro Pro
 65                  70                  75                  80

Gly Gln Ile Arg Glu Pro Thr Gly Ser Asp Ile Ala Gly Thr Thr Ser
                85                  90                  95

Thr Gln Gln Glu Gln Val His Trp Ile Thr Arg Pro Asn Asn Pro Ile
                100                 105                 110

Pro Val Gly Asp Ile Tyr Arg Lys Trp Ile Val Leu Gly Leu Asn Lys
                115                 120                 125

Met Val Lys Met Tyr
        130
```

(2) INFORMATION FOR SEQ ID NO:45:

(i) SEQUENCE CHARACTERISTICS:
        (A) LENGTH: 133 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:45:

```
Ala Leu Ser Pro Arg Thr Leu Asn Ala Trp Val Lys Ala Val Glu Glu
 1               5                  10                  15

Lys Ala Phe Asn Pro Glu Ile Ile Pro Met Phe Met Ala Leu Ser Glu
                20                  25                  30
```

Gly Ala Val Pro Tyr Asp Ile Asn Thr Met Leu Asn Ala Ile Gly Gly
            35                  40                  45

His Gln Gly Ala Leu Gln Val Leu Lys Glu Val Ile Asn Glu Glu Ala
        50                  55                  60

Ala Glu Trp Asp Arg Thr His Pro Pro Ala Met Gly Pro Leu Pro Pro
65                  70                  75                  80

Gly Gln Ile Arg Asp Pro Thr Gly Ser Asp Ile Ala Gly Thr Thr Ser
                85                  90                  95

Thr Gln Gln Glu Gln Ile Asn Trp Ile Thr Arg Pro Asn Asn Pro Val
            100                 105                 110

Pro Val Gly Asp Ile Tyr Arg Lys Trp Ile Val Leu Gly Leu Asn Lys
                115                 120                 125

Met Val Lys Leu Tyr
        130

(2) INFORMATION FOR SEQ ID NO:46:

(i) SEQUENCE CHARACTERISTICS:
        (A) LENGTH: 133 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:46:

Ala Leu Ser Pro Arg Thr Leu Asn Ala Trp Val Lys Ala Val Glu Glu
1               5                   10                  15

Lys Ala Phe Asn Pro Glu Ile Ile Pro Met Phe Met Ala Leu Ser Glu
            20                  25                  30

Gly Ala Ile Ser Tyr Asp Ile Asn Thr Met Leu Asn Ala Ile Gly Gly
            35                  40                  45

His Gln Gly Ala Leu Gln Val Leu Lys Glu Val Ile Asn Glu Glu Ala
        50                  55                  60

Ala Glu Trp Asp Arg Thr His Pro Ile Pro Val Gly Pro Leu Pro Pro
65                  70                  75                  80

Gly Gln Ile Arg Asp Pro Thr Gly Ser Asp Ile Ala Gly Thr Thr Ser
                85                  90                  95

Thr Gln Gln Glu Gln Val His Trp Thr Thr Arg Pro Asn Asn Pro Ile
            100                 105                 110

Pro Val Gly Asp Ile Tyr Arg Lys Trp Ile Val Leu Gly Leu Asn Lys
                115                 120                 125

Met Val Lys Met Tyr
        130

(2) INFORMATION FOR SEQ ID NO:47:

(i) SEQUENCE CHARACTERISTICS:
        (A) LENGTH: 133 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:47:

Ala Leu Ser Pro Arg Thr Leu Asn Ala Trp Val Ile Ala Val Glu Glu
1               5                   10                  15

Lys Ala Phe Asn Pro Glu Ile Ile Pro Met Phe Met Ala Leu Ser Glu
            20                  25                  30

```
Gly Ala Val Pro Tyr Asp Ile Asn Thr Met Leu Asn Ala Ile Gly Gly
            35                  40                  45

His Gln Gly Ala Leu Gln Val Leu Lys Glu Val Ile Asn Glu Glu Ala
        50                  55                  60

Ala Asp Trp Asp Arg Thr His Pro Pro Val Gly Pro Leu Pro Pro
65                  70                  75                  80

Gly Gln Ile Arg Glu Pro Thr Gly Ser Asp Ile Ala Gly Thr Thr Ser
                85                  90                  95

Thr Gln Gln Glu Gln Ile His Trp Ile Thr Arg Gly Gly Asn Ser Ile
            100                 105                 110

Pro Val Gly Asp Ile Tyr Arg Lys Trp Ile Val Leu Gly Leu Asn Lys
            115                 120                 125

Met Val Lys Met Tyr
        130

(2) INFORMATION FOR SEQ ID NO:48:

(i) SEQUENCE CHARACTERISTICS:
        (A) LENGTH: 133 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:48:

Pro Leu Ser Pro Arg Thr Leu Asn Ala Trp Val Lys Ala Val Glu Glu
1               5                   10                  15

Lys Ala Phe Asn Pro Glu Ile Ile Pro Met Phe Met Ala Leu Ser Glu
            20                  25                  30

Gly Ala Ile Pro Tyr Asp Ile Asn Thr Met Leu Asn Ala Ile Gly Gly
            35                  40                  45

His Gln Gly Ala Leu Gln Val Leu Lys Glu Val Ile Asn Glu Glu Ala
        50                  55                  60

Ala Asp Trp Asp Arg Thr His Pro Pro Ile Gly Pro Leu Pro Pro
65                  70                  75                  80

Gly Gln Ile Arg Glu Pro Thr Gly Ser Asp Ile Ala Gly Thr Thr Ser
                85                  90                  95

Thr Gln Gln Glu Gln Val His Trp Ile Thr Arg Ala Asn Gln Ser Ile
            100                 105                 110

Pro Val Gly Asp Ile Tyr Arg Lys Trp Ile Val Leu Gly Leu Asn Lys
            115                 120                 125

Met Val Lys Met Tyr
        130

(2) INFORMATION FOR SEQ ID NO:49:

(i) SEQUENCE CHARACTERISTICS:
        (A) LENGTH: 133 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:49:

Pro Leu Ser Pro Arg Thr Leu Asn Ala Trp Val Lys Ala Val Glu Glu
1               5                   10                  15

Lys Ala Phe Asn Pro Glu Ile Ile Pro Met Phe Met Ala Leu Ser Glu
```

```
                20              25              30
Gly Ala Ile Pro Tyr Asp Ile Asn Thr Met Leu Asn Ala Ile Gly Gly
                    35                      40                      45

His Gln Gly Ala Leu Gln Val Leu Lys Glu Val Ile Asn Glu Glu Ala
    50                      55                      60

Ser Asp Trp Asp Arg Thr His Pro Pro Ile Gly Pro Leu Pro Pro
65                      70                      75                      80

Gly Gln Ile Arg Glu Pro Thr Gly Ser Asp Ile Ala Gly Thr Thr Ser
                85                      90                      95

Thr Gln Gln Glu Gln Val His Trp Thr Thr Arg Pro Asn Gln Pro Ile
                    100                     105                     110

Pro Val Gly Asp Ile Tyr Arg Lys Trp Ile Val Leu Gly Leu Asn Lys
                    115                     120                     125

Met Val Lys Met Tyr
    130
```

(2) INFORMATION FOR SEQ ID NO:50:

(i) SEQUENCE CHARACTERISTICS:
        (A) LENGTH: 282 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:50:

```
TGTACACATG GCATCAAACC AACAGTGAGT ACTCACCTAA TATTAAATGG GACACTCTCT      60
GAAGGAAAAA TAAGAATTAT GGGAAAAAAT ATCTCGGACA CTGGGAAAAA TATCATAGTG     120
ACCCTAAATT CTACTATAAA CATAACCTGT GTGAGACCAT GGAATCAGAC AGTACAAACG     180
ATAGGAATAG GACCAATGTC CTGGCTCAGC ATGGACAAA ATGCAGATAA AAACAATAAC     240
TCAAGAATAG CTTATTGCGA GTATAACACC ACGGATTGGG AA                       282
```

(2) INFORMATION FOR SEQ ID NO:51:

(i) SEQUENCE CHARACTERISTICS:
        (A) LENGTH: 279 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:51:

```
TGTACACATG GCATCAAGCC CACAGTGAGC ACCCACCTGA TATTAAATGG GACACTCTCT      60
GAAGGAAAAA TAAGAATTAT GGGAAAAAAC ATTTCAGATA ATGCGAAAAA TATCATAGTG     120
ACCCTAAAAC AGACTATAAG CATAACTTGT GAGAGACCAG GAAATCTTTC AGTACAAGAG     180
ATAAAAATAG GTCCAATGGC CTGGTACAGC ATGGCCGTAG AGCAAGATAA GTCAACCTCC     240
AGGACAGCTT ATTGCAAGTA TAATGTCACT AAGTGGAAA                            279
```

(2) INFORMATION FOR SEQ ID NO:52:

(i) SEQUENCE CHARACTERISTICS:
        (A) LENGTH: 282 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:52:

```
TGTACACATG GCATCAAGCC AACAGTAAGT ACTCAGTTAA TATTAAATGG AACACTCTCG      60

GAAGGAAAGA TAAGAATAAT GGCAAAAGAT ATTTTAAATA GTGGCAAAAA TATCATAGTG     120

ACCCTAAATA CTACTGTAAA CATGACCTGC GTGAGACCAG GAAATATAAC AATACAAACG     180

TTAAAGATAG GTCCACTGGC CTGGTACAGC ATGGACATAG CGAATGAAAA AGACCATAAG     240

TCAAGAACAG CTTATTGTGA GTATAATACC ACTAATTGGG TA                       282
```

(2) INFORMATION FOR SEQ ID NO:53:

(i) SEQUENCE CHARACTERISTICS:
        (A) LENGTH: 279 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:53:

```
TGTACACATG GCATCAAGCC AACAGTAAGT ACTCAGCTAA TATTAAATAG AACACTCTCG      60

GAAGGAAAGA TAAAAATAAT GACAAAAAAT ATTTCGGAGA ATGGAAATAT TATAGTGACC     120

CTAAATACTA CTATAAACAT GACCTGCGAG AGACCAGGAA ATCTATCAGT ACAAGAGATA     180

AACATAGGTC CACTGGCCTG GTACAGCATG AGCATAAAGA ATGAAGGAAA AACTGAGTCA     240

AGAGTAGCTT ATTGTGAGTA TAACAGCACT AATTGGGTA                            279
```

(2) INFORMATION FOR SEQ ID NO:54:

(i) SEQUENCE CHARACTERISTICS:
        (A) LENGTH: 120 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:54:

```
AGACAACTCC GAGCTCGCCT GCTAGCCTTA GAAACCTTAA TACAGAATCA GCAACTCCTA      60

AACCTATGGG GCTGTAAGGG AAGGCTGGTC TGTTACACAT CAGTAAAATG GAACATGTCA     120
```

(2) INFORMATION FOR SEQ ID NO:55:

(i) SEQUENCE CHARACTERISTICS:
        (A) LENGTH: 120 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:55:

```
AGACAACTCC GAGCTCGCCT GCTAGCCTTA GAAACCTTAA TACAGAATCA GCAACTCCTA      60

AACCTATGGG GCTGTAAGGG AAGACTAATC TGCTACACAT CAGTAAAATG GAACTCGACA     120
```

(2) INFORMATION FOR SEQ ID NO:56:

(i) SEQUENCE CHARACTERISTICS:
        (A) LENGTH: 119 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:56:

| | | |
|---|---|---|
| AGACAACTCC GAGCTCGCCT GCTAGCCTTA GAAACCTTAA TACAGAATCA GCAACTCCTA | 60 | |
| AACTCGTGGG GCTGTTGGGA AGACTAGTCT GTTACACATC AGTAGAATGG AACTGGACA | 119 | |

(2) INFORMATION FOR SEQ ID NO:57:

(i) SEQUENCE CHARACTERISTICS:
        (A) LENGTH: 120 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:57:

| | |
|---|---|
| AGACAACTCC GAGCTCGCCT GCTAGCCTTA GAAACCTTAA TTCAGAATCA GCAACTCCTA | 60 |
| AACTCGTGGG GCTGTAAGGG AAGACAAGTC TGTTACACAT CAGTAAAATG GAACAATACA | 120 |

(2) INFORMATION FOR SEQ ID NO:58:

(i) SEQUENCE CHARACTERISTICS:
        (A) LENGTH: 399 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:58:

| | |
|---|---|
| GCCCTCTCCC CCAGGACTTT AAATGCATGG GTAAAGGCAG TAGAAGAAAA GGCCTTTAAC | 60 |
| CCGGAAATCA TTCCTATGTT CATGGCATTG TCAGAGGGAG CTGTTCCCTA TGATATTAAT | 120 |
| ACTATGCTAA ATGCCATAGG AGGACATCAA GGAGCATTAC AAGTGCTAAA GAAGTAATC | 180 |
| AATGAGGAAG CAGCAGAGTG GGATAGAACT CACCCACAAG CAGTAGGGCC ATTGCCACCA | 240 |
| GGACAGATAA GGGAACCAAC AGGAAGTGAC ATTGCTGGAA CAACCAGTAC CCAGCAAGAG | 300 |
| CAAATTCACT GGACTACCAG GGCCAACCCC CCTATCCCAG TAGGAGACAT CTATAGAAAA | 360 |
| TGGATAGTGT TAGGGCTAAA CAAAATGGTA AAAATGTAC | 399 |

(2) INFORMATION FOR SEQ ID NO:59:

(i) SEQUENCE CHARACTERISTICS:
        (A) LENGTH: 399 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:59:

| | |
|---|---|
| GCCCTCTCCC CCAGGACTTT AAATGCATGG GTAAAGGCAG TAGAAGAAAA GGCCTTTAAC | 60 |
| CCTGAAATCA TTCCTATGTT CATGGCATTA TCAGAGGGAG CTATTTCCTA TGATATTAAT | 120 |
| ACCATGCTAA ATGCCATAGG AGGACATCAA GGGGCTCTAC AGGTGCTAAA GGAAGTAATC | 180 |
| AATGAAGAAG CAGCAGATTG GGATAGAGCT CACCCACCAG TGGTAGGGCC GTTGGCACCA | 240 |
| GGGCAGATGA GGGACCCAAC AGGAAGTGAC ATCGCTGGGA CAACTAGCAC CCAGCAAGAG | 300 |
| CAAATTCATT GGACTACCAG GCCCAACAAC CCTATCCCAG TAGGAGACAT CTATAGAAAA | 360 |
| TGGATAGTGT TAGGACTAAA CAAAATGGTA AAAATGTAC | 399 |

(2) INFORMATION FOR SEQ ID NO:60:

(i) SEQUENCE CHARACTERISTICS:
        (A) LENGTH: 397 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:60:

```
GCCATTTCCC CTAGGACTTT AAATGCATGG GTAAAGGCAG TAGAAGAAAA AGCCTTTAAC      60

CCTAAAATCA TTCCTATGTT CATGGCATTG TCAGAGGGAG CTGTTCCCTA TGATATTAAT     120

ACTATGCTAA ATGCCATAGG AGGACATCAA GGGGCTTTAC AAGTGCTAAA GGAAGTAATC     180

AATGAGGAAG CATCGGAGTG GGATAGAACT CACCCACCAC CGATAGGGCC GTTACCACCA     240

GGCAGATAAG GGACCCAACA GGAAGTGACA TTGCTGGACA ACTAGCACCC AGCAAGAGCA     300

AGTTCACTGG ATTACCAGGG CCCCCAACCC TATCCCAGTA GGAGACATCT ATAGAAAATG     360

GATAGTGTTG GGACTAAACA AAATGGTAAA AATGTAC                              397
```

(2) INFORMATION FOR SEQ ID NO:61:

(i) SEQUENCE CHARACTERISTICS:
        (A) LENGTH: 399 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:61:

```
GCCATTTCCC CTAGGACTCT AAATGCATGG GTAAAGGCAG TAGAAGAAAA GGCCTTTAAC      60

CCTGAAATCA TTCCTATGTT CATGGCATTG TCAGAGGGAG CTATTCCCTA TGATATTAAT     120

ACCATGCTAA ATGCCATAGG AGGACATCAA GGGGCTTTAC AAGTGCTAAA GGAAGTAATC     180

AATGAGGAAG CATCAGAATG GGATAGAACT CACCCACAAC AGGCAGGGCC GTTACCACCA     240

GGGCAGATAA GGGACCCAAC AGGAAGTGAC ATTGCTGGGA CAACTAGCAC CCAGCAAGAG     300

CAAGTTCACT GGACTACCAG GCCGCCAAC CCTATCCCAG TAGGAGACAT CTATAGAAAA      360

TGGATAGTGT TGGGACTAAT CAAAATGGTA AAAATGTAC                            399
```

(2) INFORMATION FOR SEQ ID NO:62:

(i) SEQUENCE CHARACTERISTICS:
        (A) LENGTH: 94 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:62:

```
Cys Thr His Gly Ile Lys Pro Thr Val Ser Thr His Leu Ile Leu Asn
 1               5                  10                  15

Gly Thr Leu Ser Glu Gly Lys Ile Arg Ile Met Gly Lys Asn Ile Ser
                20                  25                  30

Asp Thr Gly Lys Asn Ile Ile Val Thr Leu Asn Ser Thr Ile Asn Ile
            35                  40                  45

Thr Cys Val Arg Pro Trp Asn Gln Thr Val Gln Thr Ile Gly Ile Gly
        50                  55                  60
```

```
Pro Met Ser Trp Leu Ser Met Asp Ile Asn Ala Asp Lys Asn Asn Asn
65                  70                  75                  80

Ser Arg Ile Ala Tyr Cys Glu Tyr Asn Thr Thr Asp Trp Glu
                85                  90
```

(2) INFORMATION FOR SEQ ID NO:63:

(i) SEQUENCE CHARACTERISTICS:
        (A) LENGTH: 93 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:63:

```
Cys Thr His Gly Ile Lys Pro Thr Val Ser Thr His Leu Ile Leu Asn
1                   5                   10                  15

Gly Thr Leu Ser Glu Gly Lys Ile Arg Ile Met Gly Lys Asn Ile Ser
                20                  25                  30

Asp Asn Ala Lys Asn Ile Ile Val Thr Leu Lys Gln Thr Ile Ser Ile
                35                  40                  45

Thr Cys Glu Arg Pro Gly Asn Leu Ser Val Gln Glu Ile Lys Ile Gly
50                  55                  60

Pro Met Ala Trp Tyr Ser Met Ala Val Glu Gln Asp Lys Ser Thr Ser
65                  70                  75                  80

Arg Thr Ala Tyr Cys Lys Tyr Asn Val Thr Lys Trp Lys
                85                  90
```

(2) INFORMATION FOR SEQ ID NO:64:

(i) SEQUENCE CHARACTERISTICS:
        (A) LENGTH: 94 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:64:

```
Cys Thr His Gly Ile Lys Pro Thr Val Ser Thr Gln Leu Ile Leu Asn
1                   5                   10                  15

Gly Thr Leu Ser Glu Gly Lys Ile Arg Ile Met Ala Lys Asp Ile Leu
                20                  25                  30

Asn Ser Gly Lys Asn Ile Ile Val Thr Leu Asn Thr Val Asn Met
                35                  40                  45

Thr Cys Val Arg Pro Gly Asn Ile Thr Ile Gln Thr Leu Lys Ile Gly
50                  55                  60

Pro Leu Ala Trp Tyr Ser Met Asp Ile Ala Asn Glu Lys Asp His Lys
65                  70                  75                  80

Ser Arg Thr Ala Tyr Cys Glu Tyr Asn Thr Thr Asn Trp Val
                85                  90
```

(2) INFORMATION FOR SEQ ID NO:65:

(i) SEQUENCE CHARACTERISTICS:
        (A) LENGTH: 93 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:65:

Cys Thr His Gly Ile Lys Pro Thr Val Ser Thr Gln Leu Ile Leu Asn
1               5                   10                  15

Arg Thr Leu Ser Glu Gly Lys Ile Lys Ile Met Thr Lys Asn Ile Ser
                20                  25                  30

Glu Asn Gly Asn Ile Ile Val Thr Leu Asn Thr Thr Ile Asn Met Thr
                35                  40                  45

Cys Glu Arg Pro Gly Asn Leu Ser Val Gln Glu Ile Asn Ile Gly Pro
    50                  55                  60

Leu Ala Trp Tyr Ser Met Ser Ile Lys Asn Glu Gly Lys Thr Glu Ser
65                  70                  75                  80

Arg Val Ala Tyr Cys Glu Tyr Asn Ser Thr Asn Trp Val
                85                  90

(2) INFORMATION FOR SEQ ID NO:66:

(i) SEQUENCE CHARACTERISTICS:
        (A) LENGTH: 42 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:66:

Arg Gln Leu Arg Ala Arg Leu Leu Ala Leu Glu Thr Leu Ile Gln Asn
1               5                   10                  15

Gln Gln Leu Leu Asn Leu Trp Gly Cys Lys Gly Arg Leu Val Cys Tyr
                20                  25                  30

Thr Ser Val Lys Trp Asn Met Ser Trp Ala
                35                  40

(2) INFORMATION FOR SEQ ID NO:67:

(i) SEQUENCE CHARACTERISTICS:
        (A) LENGTH: 41 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:67:

Arg Gln Leu Arg Ala Arg Leu Leu Ala Leu Glu Thr Leu Ile Gln Asn
1               5                   10                  15

Gln Gln Leu Leu Asn Leu Trp Gly Cys Lys Gly Arg Leu Ile Cys Tyr
                20                  25                  30

Thr Ser Val Lys Trp Asn Ser Thr Trp
                35                  40

(2) INFORMATION FOR SEQ ID NO:68:

(i) SEQUENCE CHARACTERISTICS:
        (A) LENGTH: 40 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:68:

Arg Gln Leu Arg Ala Arg Leu Leu Ala Leu Glu Thr Leu Ile Gln Asn
1               5                   10                  15

-continued

Gln Gln Leu Leu Asn Ser Trp Gly Cys Lys Gly Arg Leu Val Cys Tyr
            20                  25                  30

Thr Ser Val Glu Trp Asn Trp Thr
        35              40

(2) INFORMATION FOR SEQ ID NO:69:

(i) SEQUENCE CHARACTERISTICS:
        (A) LENGTH: 41 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:69:

Arg Gln Leu Arg Ala Arg Leu Leu Ala Leu Glu Thr Leu Ile Gln Asn
1               5                   10                  15

Gln Gln Leu Leu Asn Ser Trp Gly Cys Lys Gly Arg Gln Val Cys Tyr
            20                  25                  30

Thr Ser Val Lys Trp Asn Asn Thr Trp
        35              40

(2) INFORMATION FOR SEQ ID NO:70:

(i) SEQUENCE CHARACTERISTICS:
        (A) LENGTH: 133 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:70:

Ala Leu Ser Pro Arg Thr Leu Asn Ala Trp Val Lys Ala Val Glu Glu
1               5                   10                  15

Lys Ala Phe Asn Pro Glu Ile Ile Pro Met Phe Met Ala Leu Ser Glu
            20                  25                  30

Gly Ala Val Pro Tyr Asp Ile Asn Thr Met Leu Asn Ala Ile Gly Gly
        35                  40                  45

His Gln Gly Ala Leu Gln Val Leu Lys Glu Val Ile Asn Glu Glu Ala
    50                  55                  60

Ala Glu Trp Asp Arg Thr His Pro Gln Ala Val Gly Pro Leu Pro Pro
65                  70                  75                  80

Gly Gln Ile Arg Glu Pro Thr Gly Ser Asp Ile Ala Gly Thr Thr Ser
                85                  90                  95

Thr Gln Gln Glu Gln Ile His Trp Thr Thr Arg Ala Asn Pro Pro Ile
            100                 105                 110

Pro Val Gly Asp Ile Tyr Arg Lys Trp Ile Val Leu Gly Leu Asn Lys
        115                 120                 125

Met Val Lys Met Tyr
    130

(2) INFORMATION FOR SEQ ID NO:71:

(i) SEQUENCE CHARACTERISTICS:
        (A) LENGTH: 133 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:71:

Ala Leu Ser Pro Arg Thr Leu Asn Ala Trp Val Lys Ala Val Glu Glu
1               5                   10                  15

Lys Ala Phe Asn Pro Glu Ile Ile Pro Met Phe Met Ala Leu Ser Glu
            20                  25                  30

Gly Ala Ile Ser Tyr Asp Ile Asn Thr Met Leu Asn Ala Ile Gly Gly
            35                  40                  45

His Gln Gly Ala Leu Gln Val Leu Lys Glu Val Ile Asn Glu Glu Ala
    50                  55                  60

Ala Asp Trp Asp Arg Ala His Pro Pro Val Val Gly Pro Leu Ala Pro
65                  70                  75                  80

Gly Gln Met Arg Asp Pro Thr Gly Ser Asp Ile Ala Gly Thr Thr Ser
                85                  90                  95

Thr Gln Gln Glu Gln Ile His Trp Thr Thr Arg Pro Asn Asn Pro Ile
                100                 105                 110

Pro Val Gly Asp Ile Tyr Arg Lys Trp Ile Val Leu Gly Leu Asn Lys
                115                 120                 125

Met Val Lys Met Tyr
        130

(2) INFORMATION FOR SEQ ID NO:72:

(i) SEQUENCE CHARACTERISTICS:
        (A) LENGTH: 133 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:72:

Ala Ile Ser Pro Arg Thr Leu Asn Ala Trp Val Lys Ala Val Glu Glu
1               5                   10                  15

Lys Ala Phe Asn Pro Glu Ile Ile Pro Met Phe Met Ala Leu Ser Glu
            20                  25                  30

Gly Ala Val Pro Tyr Asp Ile Asn Thr Met Leu Asn Ala Ile Gly Gly
            35                  40                  45

His Gln Gly Ala Leu Gln Val Leu Lys Glu Val Ile Asn Glu Glu Ala
    50                  55                  60

Ser Glu Trp Asp Arg Thr His Pro Pro Ile Gly Pro Leu Pro Pro
65                  70                  75                  80

Gly Gln Ile Arg Asp Pro Thr Gly Ser Asp Ile Ala Gly Thr Thr Ser
                85                  90                  95

Thr Gln Gln Glu Gln Val His Trp Ile Thr Arg Ala Pro Asn Pro Ile
                100                 105                 110

Pro Val Gly Asp Ile Tyr Arg Lys Trp Ile Val Leu Gly Leu Asn Lys
                115                 120                 125

Met Val Lys Met Tyr
        130

(2) INFORMATION FOR SEQ ID NO:73:

(i) SEQUENCE CHARACTERISTICS:
        (A) LENGTH: 133 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:73:

Ala Ile Ser Pro Arg Thr Leu Asn Ala Trp Val Lys Ala Val Glu Glu
1               5                   10                  15

Lys Ala Phe Asn Pro Glu Ile Ile Pro Met Phe Met Ala Leu Ser Glu
                20                  25                  30

Gly Ala Ile Pro Tyr Asp Ile Asn Thr Met Leu Asn Ala Ile Gly Gly
            35                  40                  45

His Gln Gly Ala Leu Gln Val Leu Lys Glu Val Ile Asn Glu Glu Ala
        50                  55                  60

Ser Glu Trp Asp Arg Thr His Pro Gln Gln Ala Gly Pro Leu Pro Pro
65                  70                  75                  80

Gly Gln Ile Arg Asp Pro Thr Gly Ser Asp Ile Ala Gly Thr Thr Ser
                85                  90                  95

Thr Gln Gln Glu Gln Val His Trp Thr Thr Arg Ala Ala Asn Pro Ile
                100                 105                 110

Pro Val Gly Asp Ile Tyr Arg Lys Trp Ile Val Leu Gly Leu Ile Lys
            115                 120                 125

Met Val Lys Met Tyr
    130

(2) INFORMATION FOR SEQ ID NO:74:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "PRIMER"

(xi) SEQUENCE DESCRIPTION: SEQ ID NO:74:

CAGGGACAAA TGGTACATCA                                                   20

(2) INFORMATION FOR SEQ ID NO:75:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "PRIMER"

(xi) SEQUENCE DESCRIPTION: SEQ ID NO:75:

AGTAGCTTGC TCAGCTCTTA AT                                                22

(2) INFORMATION FOR SEQ ID NO:76:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "PRIMER"

(xi) SEQUENCE DESCRIPTION: SEQ ID NO:76:

TRGTTACTTG TACACATGGC AT                                                22

-continued (2) INFORMATION FOR SEQ ID NO:77:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(xi) SEQUENCE DESCRIPTION: SEQ ID NO:77:

ACAATAAAAG AATTCTCCAT GACAGT                        26

(2) INFORMATION FOR SEQ ID NO:78:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:78:

Asn Thr Arg Lys Ser Ile Asn Ile Gly Pro Gly Arg Ala Phe Tyr Ala
1           5                 10               15

Thr Gly Glu Ile Ile
        20

(2) INFORMATION FOR SEQ ID NO:79:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:79:

Asn Thr Arg Lys Gly Ile Asn Ile Gly Pro Gly Arg Ala Phe Tyr Thr
1           5                 10               15

Thr Gly Glu Ile Ile
        20

(2) INFORMATION FOR SEQ ID NO:80:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:80:

Arg Glu Val Gln Asp Ile Tyr Thr Gly Pro Met Arg Trp Arg Ser Met
1           5                 10               15

Thr Leu Lys Arg Ser Asn Asn Thr Ser
        20             25

(2) INFORMATION FOR SEQ ID NO:81:

(i) SEQUENCE CHARACTERISTICS:
        (A) LENGTH: 25 amino acids
        (B) TYPE: amino acid

```
        (C) STRANDEDNESS: single
        (D) TOPOLOGY: linear (ii) MOLECULE TYPE: peptide (xi) SEQUENCE DESCRIPTION: SEQ ID NO:81:

Arg Asp Ile Gln Glu Met Arg Ile Gly Pro Met Ala Trp Tyr Ser Met
1               5                   10                  15

Gly Ile Gly Gly Thr Ala Gly Asn Ser
            20                  25
```

GROUP O HIV-1, FRAGMENTS OF SUCH VIRUSES, AND USES THEREOF

This application is a divisional of application Ser. No. 08/894,699 filed Dec. 1, 1997, U.S. Pat. No. 6,030,769.

BACKGROUND OF THE INVENTION

The present invention relates to retrovirus strains of the HIV-1 group, group O, and in particular the strains called BCF02 (ESS), BCF01 (FAN), BCF06 (LOB), BCF07 (MAN), BCF08 (NKO), BCF11 (NAN) and BCF03 (POC), to fragments of the said retroviruses and to their applications as diagnostic reagent and as immunogenic agent.

Two distinct types of HIV (human immunodeficiency virus: HIV-1 and HIV-2) have been described and are the agents responsible for AIDS. Analysis of their nucleic acid sequence has made it possible to identify various subtypes of HIV-1, although no correlation could be established between variability and pathogenicity. Similarly, HIV-2 exhibits a greater genetic and biological diversity than that previously envisaged.

Analysis of nucleotide fragments of various HIV-1 isolates has shown the existence, through the analysis of the env gene, of at least 7 different subtypes, called A to G (MYERS G. et al., Human retroviruses and AIDS, 1993, Los Alamos Nat. Lab.).

More recently, two other isolates, considered to be considerably more distant from the other 7 subtypes, that is to say whose sequence homology is the most distant from that of the reference HIV-1 strains, have also been isolated: HIV-1ANT70 and HIV-1MVP5180, obtained from Cameroonian patients, and have been attached to a new HIV-1 group, group O, as opposed to group M corresponding to the 7 abovementioned A–G subtypes, taking into account their genomic organization (5' LTR Gag Pol Vif Vpu Vpr Tat Rev Env Nef LTR 3'), (Patent Application WO 89/12094, European Patent Application No. 0,591,914, GÜRTLER L. G. et al., J. Virol., 1994, 68, 1581–85).

Analysis of the DNA sequences has shown 65–70% similarity with HIV-1 and 56% with HIV-2.

By using a competition immunoblotting method, using a peptide V3 from MVP5180, a 7–8% prevalence is found in Yaoundë. This prevalence might be under-estimated since the V3 loop is known, in all the HIV-1 subtypes, to be a highly variable region. Molecular studies also indicate the presence of group O virus in Gabon, France, Spain and Germany.

Ongoing serological studies reveal group O HIV-1 infections in Nigeria, Niger and Senegal.

Knowledge of these various groups and subtypes is particularly important for developing:

reagents for screening for HIV infections which are sufficiently sensitive and specific, that is to say which do not lead to false-negative or false-positive results; and compositions which protect against all existing subtypes, including the entire group O viruses.

Indeed, it has been shown, in particular, that some detection reagents were not sufficiently sensitive and did not always make it possible to detect group O HIV-1 infections (LOUSSERT-AJAKA I. et al., Lancet, 1994, 343, 1393–94), which has led to the withdrawal of three screening kits and to the declassification of two others on the French market.

The results show that the group O viruses are very distant from the group M HIV-1 subtypes. These results indicate that the HIV-1 viruses ought to be classified in two different groups, namely: HIV-1 M and HIV-1 O. The group O viruses appear to be capable of being transmitted by horizontal and vertical routes, leading to a very wide distribution of this infection. The pathogenicity of these viruses is under study. The divergence of these viruses should be taken into account in the sensitivity of diagnostic tests and in the development of vaccines.

Consequently, the Applicant set itself the objective of providing fragments, derived from selected group O HIV-1 strains, capable of allowing both detection of the entire group O HIV-1 viruses and specific intra-group O differentiation and which are also capable of inducing protection against the entire HIV-1 subtypes, including group O, which fragments make it possible to avoid obtaining false-negative or false-positive results; to do this, the inventors selected a set of strains and sequences, derived essentially from a region of the env gene, in particular at the level of a hypervariable fragment situated in the V3 loop (C2V3) or at the level of gp41 and of a region of the gag gene.

The subject of the present invention is group O HIV-1 strains exhibiting the morphological and immunological characteristics of one of the retroviruses deposited at the Collection Nationale de Cultures de Microorganismes held by Institut Pasteur under the numbers I-1544 (called BCF02 (ESS)), I-1543 (called BCF01 (FAN)), I-1546 (called BCF07 (MAN)), I-1547 (called BCF08 (NKO)), I-1545 (called BCF03 (POC)), on the date of Feb. 24, 1995.

The subject of the present invention is also a nucleic acid fragment, characterized in that its nucleotide sequence is chosen from those which are contained in one of the nucleotide sequences included in the env or gag genes of the group O HIV-1 strains and its variants and comprises:

either one of the following sequences, included in the C2V3-env gene fragment (hypervariable loop of gp120): SEQ ID No. 1 (BCF02 (ESS)), SEQ ID No. 2 (BCF08 (NKO)), SEQ ID No. 3 (BCF03 (POC)), SEQ ID No. 4 (BCF06 (LOB)), SEQ ID No. 5 (BCF07 (MAN)), SEQ ID No. 6 (BCF01 (FAN)), SEQ ID No. 7 (BCF11 (NAN)), SEQ ID No. 50 (BCF09), SEQ ID No. 51 (BCF12), SEQ ID No. 52 (BCF13), SEQ ID No. 53 (BCF14), or one of the following sequences, included in the gp14 fragment of the env gene: SEQ ID No. 8 (BCF02 (ESS)), SEQ ID No. 9 (BCF08 (NKO)), SEQ ID No. 10 (BCF03 (POC)), SEQ ID No. 11 (BCF06 (LOB)), SEQ ID No. 12 (BCF07 (MAN)), SEQ ID No. 13 (BCF01 (FAN)), SEQ ID No. 14 (BCF11 (NAN)), SEQ ID No. 54 (BCF09), SEQ ID No. 55 (BCF12), SEQ ID No. 56 (BCF13), SEQ ID No. 57 (BCF14), or one of the following sequences, included in the gag gene: SEQ ID No. 15 (BCF02 (ESS)), SEQ ID No. 16 (BCF08 (NKO)), SEQ ID No. 17 (BCF03 (POC)), SEQ ID No. 18 (BCF05 (LOB)), SEQ ID No. 19 (BCF07 (MAN)), SEQ ID No. 20 (BCF01 (FAN)), SEQ ID No. 21 (BCF11 (NAN)), SEQ ID No. 58 (BCF09), SEQ ID No. 59 (BCF12), SEQ ID No. 60 (BCF13), SEQ ID No. 61 (BCF14), or, if the sequence is not identical to one of the above nucleotide sequences, or is not complementary to one of these sequences, is nonetheless capable of hybridizing with a nucleic sequence derived from a group O HIV-1 virus.

For the purposes of the present invention, nucleic sequence is understood to mean the sequences, as specified above and their complementary sequences, as well as the sequences containing them.

Such sequences find application both in the specific identification of a group O HIV-1, as diagnostic reagent, alone or in a pool with other reagents, for the identification of any HIV-1 or alternatively, depending on the cases, as reagent for intra-group O differentiation.

These sequences may be used in particular in diagnostic tests comprising either a direct hybridization with the viral sequence to be detected, or an amplification of the said viral sequence, using, as primers, an oligonucleotide, included in any one of the above sequences and in particular one of the following sequences:

* sequences gag
  GAG/5'CAM or G5: CAGGGACAAATGGTACATCA (positions 1250–1269) (SEQ ID No. 74)
  GAG/3'CAM or G3: AGTAGCTTGCTCAGCTCT-TAAT (positions 1768-1747) (SEQ ID No. 75)
* sequences gp41
  SEQ ID No. 22 (gp41/5'CAM-1): AGRGAAAAA-GAGCAGTAGGAT (positions 7800–7821)
  SEQ ID No. 23 (gp41/5'CAM-2): TCTAAGTGCAG-CAGGTAGCACTAT (positions 7843–7866)
  SEQ ID No. 24 (gp41/3'CAM-2): CTAAGTTGCT-CAAGAGTGGTA (positions 8594-8573)
  SEQ ID No. 25 (gp41/3'CAM-2): GTTGCTCAAGAG-GTGGTAAGT (positions 8590-8570)
sequences C2V3:
  C2V3/5'CAM or V3L5: TRGTTACTTGTACACATG-GCAT (positions 6991–7012) (SEQ ID No. 76)
  C2V3/3'CAM or V3L3: ACAATAAAAGAATTCTC-CATGACAGT (positions 7421-7396) (SEQ ID No. 77).

The abovementioned positions correspond to those of the Ant70 sequence (Myers, Korber et al., cited above).

The subject of the present invention is also group O HIV-1 strains, characterized in that they comprise at least one of the sequences selected from the group consisting of the sequences SEQ ID No. 1 to SEQ ID No. 7 or SEQ ID No. 50 to SEQ ID No. 53, at least one of the sequences selected from the group consisting of the sequences SEQ ID No. 8 to SEQ ID No. 14 or SEQ ID No. 54 to SEQ ID No. 57 and at least one of the sequences selected from the group consisting of the sequences SEQ ID No. 15 to SEQ ID No. 21 or SEQ ID No. 58 to SEQ ID No. 61.

According to an advantageous embodiment of the said strain, it comprises the sequences SEQ ID No. 50, SEQ ID No. 54, SEQ ID No. 58; this strain has been called BCF09.

According to another advantageous embodiment of the said strain, it comprises the sequences SEQ ID No. 51, SEQ ID No. 55, SEQ ID No. 59; this strain has been called BCF12.

According to yet another advantageous embodiment of the said strain, it comprises the sequences SEQ ID No. 52, SEQ ID No. 56, SEQ ID No. 60; this strain has been called BCF13.

According to yet another advantageous embodiment of the said strain, it comprises the sequences SEQ ID No. 53, SEQ ID No. 57, SEQ ID No. 61; this strain has been called BCF14.

According to another advantageous embodiment of the said strain, it comprises the sequences SEQ ID No. 7, SEQ ID No. 14, SEQ ID No. 21; this strain has been called BCF11.

According to yet another advantageous embodiment of the said strain, it comprises the sequences SEQ ID No. 4, SEQ ID No. 11, SEQ ID No. 18; this strain has been called BCF06.

The subject of the invention is also the use of the sequences described above for carrying out a process of hybridization or gene amplification of nucleic sequences of the HIV-1 type, these processes being applicable to the in vitro diagnosis of the potential infection of an individual with an HIV-1 type virus, including group O.

This in vitro diagnostic method is carried out using a biological sample (serum, circulating lymphocytes) and comprises:

a step of extracting the nucleic acid to be detected, belonging to the genome of the HIV-1 type virus, which may be present in the biological sample and, where appropriate, a step of treating the nucleic acid with the aid of a reverse transcriptase, if the latter is in RNA form, at least one cycle comprising the steps of denaturation of the nucleic acid, annealing with at least one sequence in accordance with the invention and extension of the hybrid formed, in the presence of the appropriate reagents (polymerizing agent such as DNA polymerase and dNTP), and a step of detecting the possible presence of the nucleic acid belonging to the genome of a group O HIV-1 type virus (group specificity).

The subject of the invention is also a peptide characterized in that it is expressed by a nucleotide sequence as defined above.

Among these peptides, there may be mentioned in particular:

those expressed by the C2V3-env gene fragment in accordance with the invention: SEQ ID No. 26 (BCF02 (ESS)), SEQ ID No. 27 (BCF01 (FAN)), SEQ ID No. 28 (BCF01 (FAN)), SEQ ID No. 29 (BCF06 (LOB)), SEQ ID No. 30 (BCF07 (MAN)), SEQ ID No. 31 (BCF11 (NAN)), SEQ ID No. 32 (BCF08 (NKO)), SEQ ID No. 33 (BCF08 (NKO)), SEQ ID No. 34 (BCF03 (POC)), SEQ ID No. 35 (BCF03 (POC)), SEQ ID No. 62 (BCF09), SEQ ID No. 63 (BCF12), SEQ ID No. 64 (BCF13), SEQ ID No. 65 (BCF14), those expressed by the gp41 env gene fragment in accordance with the invention: SEQ ID No. 36 (BCF02 (ESS)), SEQ ID No. 37 (BCF01 (FAN)), SEQ ID No. 38 (BCF06 (LOB)), SEQ ID No. 39 (BCF07 (MAN)), SEQ ID No. 40 (BCF08 (NKO)), SEQ ID No. 41 (BCF03 (POC)), SEQ ID No. 42 (BCF11 (NAN)), SEQ ID No. 66 (BCF09), SEQ ID No. 67 (BCF12), SEQ ID No. 68 (BCF13), SEQ ID No. 69 (BCF14), those expressed by the gag gene fragment in accordance with the invention: SEQ ID No. 43 (BCF02 (ESS)), SEQ ID No. 44 (BCF01 (FAN)), SEQ ID No. 45 (BCF06 (LOB)), SEQ ID No. 46 (BCF07 MAN)), SEQ ID No. 47 (BCF11 (NAN)), SEQ ID No. 48 (BCF08

(NKO)), SEQ ID No. 49 (BCF03 (POC)), SEQ ID No. 70 (BCF09), SEQ ID No. 71 (BCF12), SEQ ID No. 72 (BCF13), SEQ ID No. 73 (BCF14).

The subject of the invention is also immunogenic compositions comprising one or more products of translation of the nucleotide sequences according to the invention or a fragment thereof and/or at least one of the peptides as defined above.

The subject of the invention is also the antibodies directed against one or more of the peptides described above and their use for carrying out methods of in vitro diagnosis of the infection of an individual with an HIV-1 type virus, according to processes known to persons skilled in the art.

By way of illustration, such an in vitro diagnostic method according to the invention comprises bringing a biological sample collected from a patient into contact with antibodies according to the invention, and detecting, with the aid of any appropriate process, in particular with the aid of anti-labelled immunoglobulins, the immunological complexes formed between the antigens of the HIV-1 type viruses which may be present in the biological sample and the said antibodies.

The subject of the present invention is also a process for screening and typing group O HIV-1, characterized in that it comprises bringing any of the nucleotide fragments in accordance with the invention into contact with the nucleic acid of the virus to be typed and detecting the hybrid formed.

In addition to the preceding arrangements, the invention further comprises other arrangements, which will emerge from the description which follows, which refers to examples for carrying out the process which is the subject of the present invention as well as to the accompanying drawings, in which:

Figure 1:
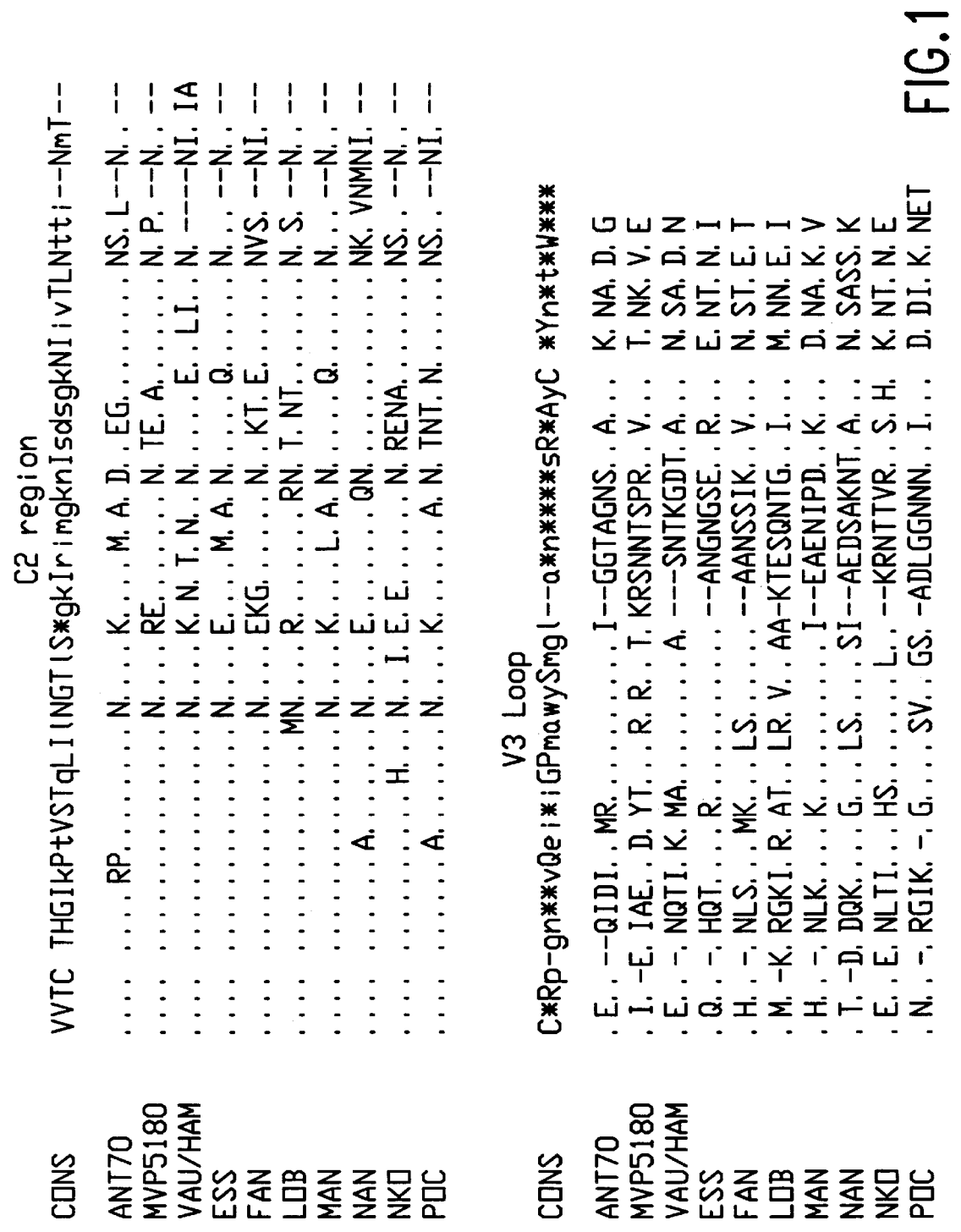

FIG. 1 represents the compared sequences of amino acids expressed by the env C2V3 gene fragment;

FIG. 2 represents the compared sequences of amino acids expressed by the gag gene fragment;

Figures 3, 4:
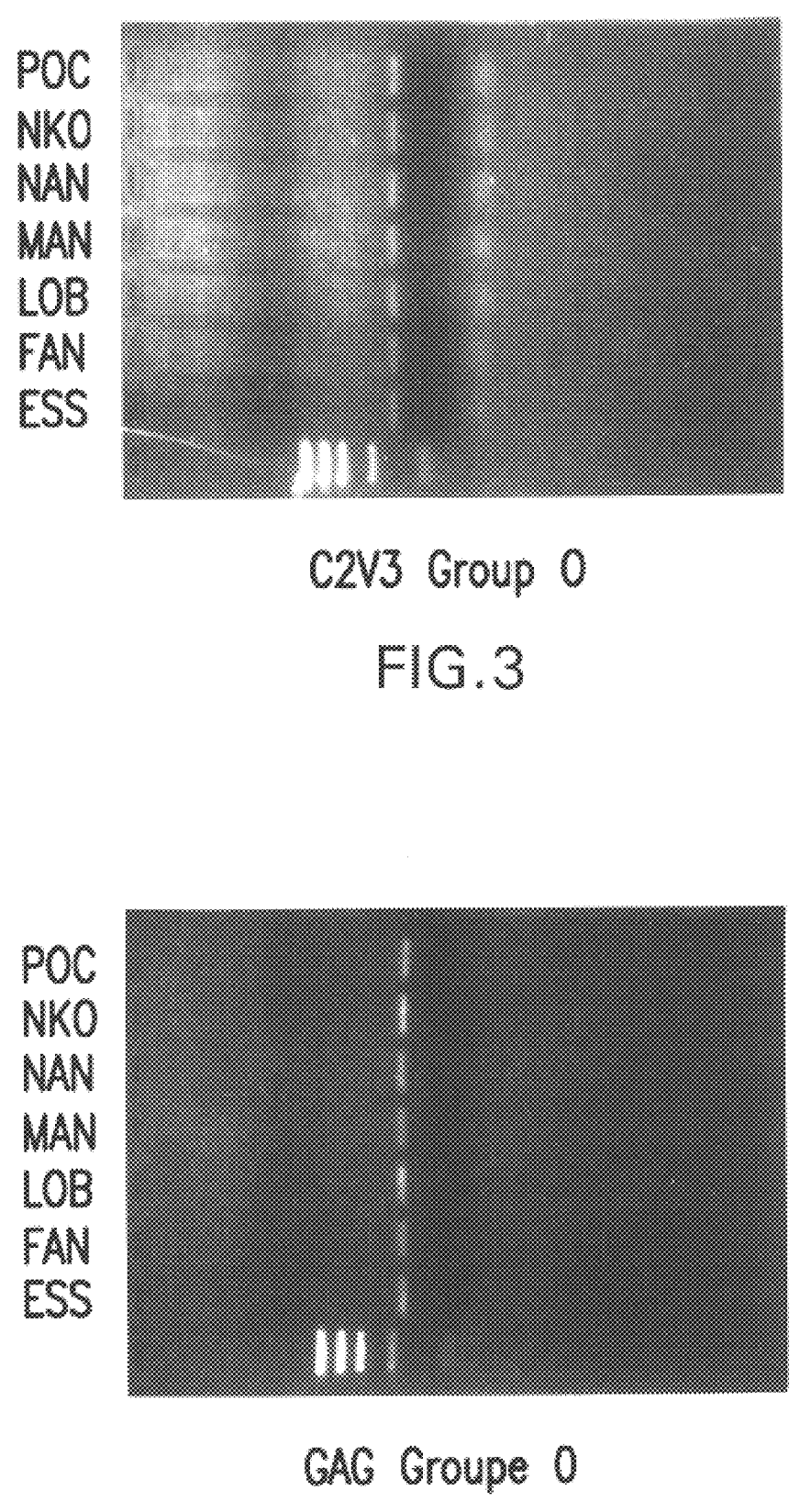

FIG. 3 illustrates the results obtained with the 7 strains BCF02 (ESS), BCF01 (FAN), BCF07 (MAN), BCF11 (NAN), BCF08 (NKO), BCF03 (POC) and BCF06 (LOB) on agarose gel, of a PCR carried out with the abovementioned C2V3 primers;

FIG. 4 illustrates the results obtained with the 7 strains BCF02 (ESS), BCF01 (FAN), BCF07 (MAN), BCF11 (NAN), BCF08 (NKO), BCF03 (POC) and BCF06 (LOB) on agarose gel, of a PCR carried out with the abovementioned Gag primers;

FIG. 5 represents the markers used in FIGS. 3 and 4;

Figure 6:
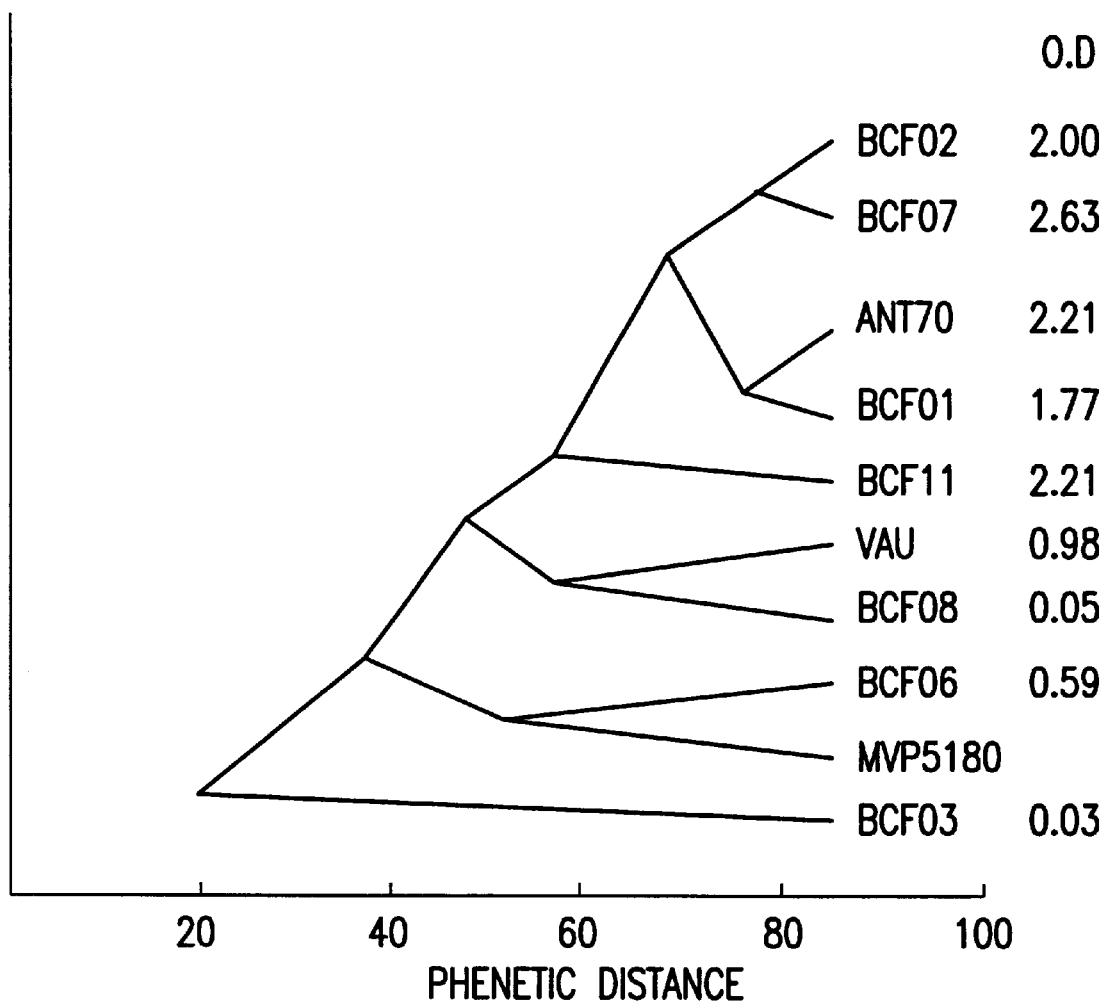
FIG. 6 illustrates the reactivity of the sera corresponding to the strains according to the invention, relative to the phenetic organization of these variants.

It should be understood, however, that these examples are given solely by way of illustration of the subject of the invention and do not in any way constitute a limitation thereto.

EXAMPLE 1

Production of the Sequences in Accordance with the Invention

Patients

Seven Cameroonian patients, consulting or hospitalized in Paris hospitals are included in this study.

At the time of diagnosis of the seropositive state, four patients are at the AIDS stage (CDC IVA n=1, CDC IVC1 n=3) and 3 patients are asymptomatic (CDC LI). The age group varies between 22 and 44 years for the symptomatic patients and it ranges between 22 and 68 years for the asymptomatic patients.

Four patients have a CD4+ level<$200 \times 10^6/\mu l$ (10, 19, 91, 97), 2 patients have CD4+ levels of between 200 and $500 \times 10^6/\mu l$ (384, 420) and one patient has CD4+ levels>$500 \times 10^6/\mu l$ (575).

Cultures

Ten to twenty ml of total blood for these 7 patients were collected over lithium heparin. The peripheral blood mononuclear cells (PBMC) are isolated on a Ficoll-Hypaque centrifugation gradient (Pharmacia). The cellular pellet obtained is washed twice with RPMI 1640 and resuspended in culture medium at a concentration of $2 \times 10^6$ cells/ml. This culture medium contains RPMI 1640 supplemented with 20% foetal calf serum, 10% human interleukin, 150 $\mu$g/ml of streptomycin, 250 units/ml of penicillin G and 5% L-glutamin. One million of the patient's cells is cocultured in duplicate with one million cells from donors stimulated with PHA in 24-well culture plates (Costar). The culture medium is changed twice per week, and $3 \times 10^5$ donor cells are added to each well on d7, d14 and d21.

The viral replication is monitored in the culture supernatants for 28 days, simultaneously by a microtechnique (measurement of the reverse transcriptase activity) and the detection of the p24 antigen (ELAVIA® p24 Ag, Sanofi-Diagnostic Pasteur). The positive-culture supernatants are collected and kept at −80° C. for the reinoculations.

Preparation of the DNA

A PCR is carried out using the DNA of fresh lymphocytes extracted from a patient or of lymphocytes, after 6 days of coculture or plasma after RT. Using 100 $\mu$l of a reaction mixture, containing Tris-HCl 10 mmol/l pH 8.3, KCl 50 mmol/l, $MgCl_2$ 2 mmol/l, 0.2 mmol/l of each dNTP, 40 pmol of each primer, 2.5 U of Taq polymerase (Perkin Elmer Cetus, St Quentin Yvelines, France) and 1 $\mu$g of cellular DNA. The primers used are those specified above, namely:

* sequences gag:
  GAG/5'CAM: CAGGGACAAATGGTACATCA (positions 1250–1269) (SEQ ID No. 74); GAG/3'CAM: AGTAGCTTGCTCAGCTCTTAAT (positions 1768–1747) (SEQ ID No. 75)
* sequences gp41
  gp41/5'CAM-1: AGRGAAAAAAGAGCAGTAGGAT (positions 7800–7821) (SEQ ID No. 22)
  gp41/5'CAM-2: TCTAAGTGCAGCAGGTAGCAC-TAT (positions 7843–7866) (SEQ ID No. 23)
  gp41/3'CAM-2: CTAAGTTGCTCAAGAGTGGTA (positions 8594–8573) (SEQ ID No. 24)
  gp41/3'CAM-1: GTTGCTCAAGAGGTGGTAAGT (positions 8590–8570) (SEQ ID No. 25)
* or alternatively one of the following sequences: SEQ ID No. 76 and SEQ ID No. 77 for the env region and SEQ ID No. 74 and SEQ ID No. 75 for the gag region, corresponding respectively to nucleotides 6991–7012, 7421–7396 and 1250–1269, 1768–1747 of the HIV1$^{Ant70}$ sequence.

The samples are subjected to 40 amplification cycles, each cycle comprising the following three steps: denaturation at 94° C. for one minute, annealing of the primers at 50° C. for the gag sequence and at 55° C. for the env sequence, for one minute and extension at 72° C. for one minute. During the first cycle, the denaturation is carried out for 4 minutes and for the last cycle, the extension is carried out for 5 minutes. The amplified products are subjected to enzymatic digestion (Xho1, EcoR1), purified and cloned into a vector M13mp18, digested with the restriction enzymes Sal1 and EcoR.

For each patient, between 3 and 4 clones are sequenced (Applied 373A sequencer), in a 406-bp region of the gag gene, in a 320-bp region of the env gene included in the V3 region and at the level of the region encoding gp41.

EXAMPLE 2

Imunodotection of a Group O HIV-1

ELISA tests are carried out in microtitre plates (Falcon 3912, microtest III®, Becton Dickinson).

The wells are covered with 100 μl of one of the V3 peptides defined above: BCF08 (NKO): R T I Q E I H S G P M A W Y S L G L K R N T T V R (SEQ ID No. 33); BCF01 (FAN): R S V Q E M K I G P L S W Y S M G L A A N S S I K (SEQ ID No. 28); BCF03 (POC): R I K Q I G I G P M S V Y S G S L A D L G N N N (SEQ ID No. 35), diluted to 10 μg.ml$^{-1}$ in a 0.05 M carbonate buffer pH 9.6 by overnight incubation, at +4° C.

The plates are then washed three times with a PBS buffer containing Tween® 20 (Prolabo, France), (PBS-Tween®) 0.1%, and then they are saturated with PBS, which is supplemented with 1% milk (Gloria Co., France), for 1 h at 37° C.

Sera (1/100), diluted in a PBS-milk mixture containing Tween® 20 at 0.1% (PBS-milk-Tween ), are incubated for 2 h at 37° C.

After three washes, anti-human polyvalent antibodies, conjugated with alkaline phosphatase (Sigma), diluted 1:10,000 in PBS-milk-Tween, are added and incubated for 1 h at 37° C. After the last wash, the coloured reaction is developed at 37° C., with an alkaline phosphatase substrate, p-nitrophenylphosphate (Sigma), diluted in a 0.05 M carbonate buffer pH 9.5, containing 2 mM MgCl$_2$, in order to obtain a concentration of 1 mg.ml$^{-1}$. The absorbance, measured at 405 nm ($A_{405}$) is recorded with an apparatus (MR 5000, Dynatech). A cut-off is determined for each serum tested and corresponds to three times the $A_{405}$ value obtained with the peptide E19S, derived from *Plasmodium malariae*.

Table 1 below shows the results obtained.

The consensus and FR 15-1 sequences correspond to those obtained from the B subtype, found in France.

| | Seronegative and seropositive African patients (group M) | | | | | | | | | | | | |
|---|---|---|---|---|---|---|---|---|---|---|---|---|---|
| Peptides/Serum | 8189 | 8362 | 8364 | 8365 | 8366 | 8370 | 8429 | 8499 | 8503 | 8116 | 8122 | 8186 | 3171 |
| HIV Serology | − | − | − | − | − | − | + | + | + | + | + | + | + |
| Neg | 0.129 | 0.319 | 0.158 | 0.158 | 0.328 | 0.152 | 0.17 | 0.157 | 0.28 | 0.201 | 0.14 | 0.171 | 0.17 |
| CONS | | | | | | | 1.46 | | 0.65 | 2.52 | 1.72 | 1.92 | |
| FR15-1 | | | | | | | 2.64 | | 1.04 | 2.77 | 2.3 | 2.86 | |
| MVP5180 | | | | | | | | | | | | | |
| ANT70 | | | | | | | | | | | | | |
| BCF08 (NKO) | | | | | | | | | | | | | |
| BCF01 (FAN) | | | | | | | | | | | | | |
| BCF03 (POC) | | | | | | | | | | | | | |

| | Group O patients | | | | | | | | |
|---|---|---|---|---|---|---|---|---|---|
| Peptides/Serum | BCF06 | BCF07 | BCF01 | BCF03 | BCF09 | VAU | BCF08 | Neg | Blan |
| HIV Serology | + | + | + | + | + | + | − | | |
| Neg | 0.299 | 0.175 | 0.197 | 0.257 | 0.146 | 0.181 | 0.327 | 0.193 | 0.127 |
| CONS | | | | | | | 0.72 | | |
| FR15-1 | | | | | | | 0.67 | | |
| MVP5180 | | 0.76 | | | | | | | |
| ANT70 | | >3 | 1.83 | | | 0.5 | | | |
| BCF08 (NKO) | 0.68 | 1.76 | 1.16 | | | | | | |
| BCF01 (FAN) | 1.08 | 2.28 | 1.51 | | 0.68 | 0.59 | | | |
| BCF03 (POC) | | | | | | | | | |

Only the results greater than twice the background have been kept
Sequence of the peptides

| | |
|---|---|
| Consensus | NTRKSINIGPGRAFYATGEII |
| FR 15-1 | NTRKGINIGPGRAFYTTGEII |
| MVP5180 | REVQDIYTGPMRWRSMTLKRSNNTS |
| ANT70 | RDIQEMRIGPMAWYSMGIGGTAGNS |
| BCF08 (NKO) | RTIQEIHSGPMAWYSLGLKRNTTVR |
| BCF01 (FAN) | RSVQEMKIGPLSWYSMGLAANSSIK |
| BCF03 (POC) | RIKQIGIGPMSVYSGSLADLGNNN |

This Table I shows the specificity of the peptides according to the invention.

EXAMPLE 3

Serotype, Phenotype and Genotype Characteristics of the Strains According to the Invention These characteristics are illustrated in Tables II and III below.

TABLE II

| | SEROTYPE | | | | | | | PHENOTYPE | | |
|---|---|---|---|---|---|---|---|---|---|---|
| | Antigen E1A | | | | | V3 | | Sensitivity to antiviral agents | | |
| | HIV-1 | | | | | ANT70 | | TIBO | DELA- | SAQUINA- |
| | 1 | 2 | 3 | 4 | 5 | 6 | 7 | RO82913 | VERDINE | VIR |
| BCF01 | − | + | + | + | + | + | + | R | R | R |
| BCF02 | − | − | − | − | − | + | + | R | R | S |
| BCF03 | + | − | + | + | − | − | − | R | R | S |
| BCF06 | + | − | + | + | + | ± | + | R | R | S |
| BCF07 | + | − | − | + | + | + | + | R | R | S |
| BCF08 | + | − | + | + | + | − | ± | R | R | S |
| BCF11 | + | − | + | + | + | + | ± | R | S | R |
| VAU | + | − | + | + | + | + | + | S | S | S |

1 Test WELLCOME competition HIV-1
2 Test CLONATEC indirect HIV-1/2
3 Test ABBOTT 3rd
4 Test WELLCOME 3rd
5 Test BOEHRINGER
6 EIA ANT70 V3
7 Dot blot ANT70 V3 INNOLIA
R: Resistant
S: Sensitive

TABLE III

| | PHENOTYPE | | GENOTYPE | | | | | | | |
|---|---|---|---|---|---|---|---|---|---|---|
| | on MT2 cells | | PCR | | | | | | | |
| | SI/NSI | p24 | ROCHE | V3 LOOP SUMMIT | | | | | | |
| BCF01 | NSI | + | − | K | I | G | P | L | S | W |
| BCF02 | NSI | + | − | R | I | G | P | M | A | W |
| BCF03 | SI | + | − | G | I | G | P | M | S | V |
| BCF06 | NSI | + | − | A | T | G | P | L | R | W |
| BCF07 | NSI | + | − | K | I | G | P | M | A' | W |
| BCF08 | NSI | + | − | H | S | G | P | M | A | W |
| BCF11 | NSI/NR | − | − | G | I | G | P | L | S | W |
| VAU | Not tested | Not tested | Not tested | M | A | G | P | M | A | W |

SI: Induction of syncytia on MT2 cells
NSI: No induction of syncytia on MT2 cells
NR: Non-replicative
p24: Production (+) or absence (−) of p24 antigen on cultures of MT2 cells Serotype analysis on a set of commercialized tests (Table II) (with the exception of Test No. 6, EIA Ag V3 ANT70, non-commercialized research product) reveals the great diversity of antibody response towards the subtype B antigens which dominate in the west and relative to the antigen of the V3 loop of the ANT70 strain. The sera, corresponding to each of the isolates according to the invention, exhibit a unique and characteristic profile. BCF 01 is the only one positive on Test 2 (Clonatec®). BCF 02 is completely negative on the subtype B antigens. BCF 03, conversely, reacts with subtype B but is negative on the ANT70 antigens. BCF 07 is the only one negative on Tests No. 2 (Clonatec) and No. 3 (Abbott 3rd), but reactive on all the other tests with group M antigen. BCF 08 is strictly negative on the EIA V3 ANT70 test but, like BCF 11, is weakly reactive on this antigen by Test 7 (InnoLIA). By comparison, the serum corresponding to the VAU strain, which has been molecularly characterized by CHARNEAU et al. (Virology, 1994, 205, 247–253), is positive on all these antigens with the exception of Test 2 (Clonatec®). This diversity in antibody response should be interpreted as a reflection of the antigenic diversity of these strains. A link with immunodepression is excluded, the patients BCF 07, 08 and 11 being completely asymptomatic with a CD4 number>400/ml. FIG. 6 indicates the reactivity of the sera corresponding to the strains according to the invention relative to the phenetic organization of these variants.

The phenotype characterization of the isolates according to the invention shows the importance and the need to have a large number of sensitive reagents. All are naturally resistant to the molecule Tibo Ro82913 (Table III) as already reported for HIV-2. An absence of an in vitro growth-inhibiting activity outside a treatment with Ro82913 has never been reported for HIV-1 before. In contrast, the VAU strain is perfectly sensitive to Ro82913.

The strains are also resistant to another non-nucleoside inhibitor, Delaverdine, with the exception of the BCF 11 strain, which is sensitive.

Conversely, this strain is resistant to Saquinavir, an anti-protease, whereas the other strains are sensitive to it.

This diversity in response to the anti-retroviral agents reinforces the notion of a high dispersion right inside the Cameroon variants.

Furthermore, the results of syncytia formation on the continuous line MT2 complicates any classification since there is no correlation with the preceding serotype or genotype results and no relationship with the clinical stage. These strains do not induce syncytial formation whereas the detection of p24 antigen in the supernatants confirms the replication on this line.

Finally, at the genotype level, all the amplifications of the genomes of the strains according to the invention are negative by PCR using a kit marketed by Roche Diagnostics, which uses primers and probes corresponding to a conserved region of the HIV-1 Gag gene; a negative result was also possible for this test in the HIV-1 A subtypes (LOUSSERT-AJAKA et al., 1995, Lancet, 346, 912–913; LOUSSERT-AJAKA et al., 1995, 346, 1489). This negative result within variant isolates from Cameroon but also within the A subtypes reinforces this notion of high HIV-1 variability and shows the need for the detection of the HIV-1 nucleic acids, to use a large panel of sequences and in particular those according to the present invention.

Figure 7:
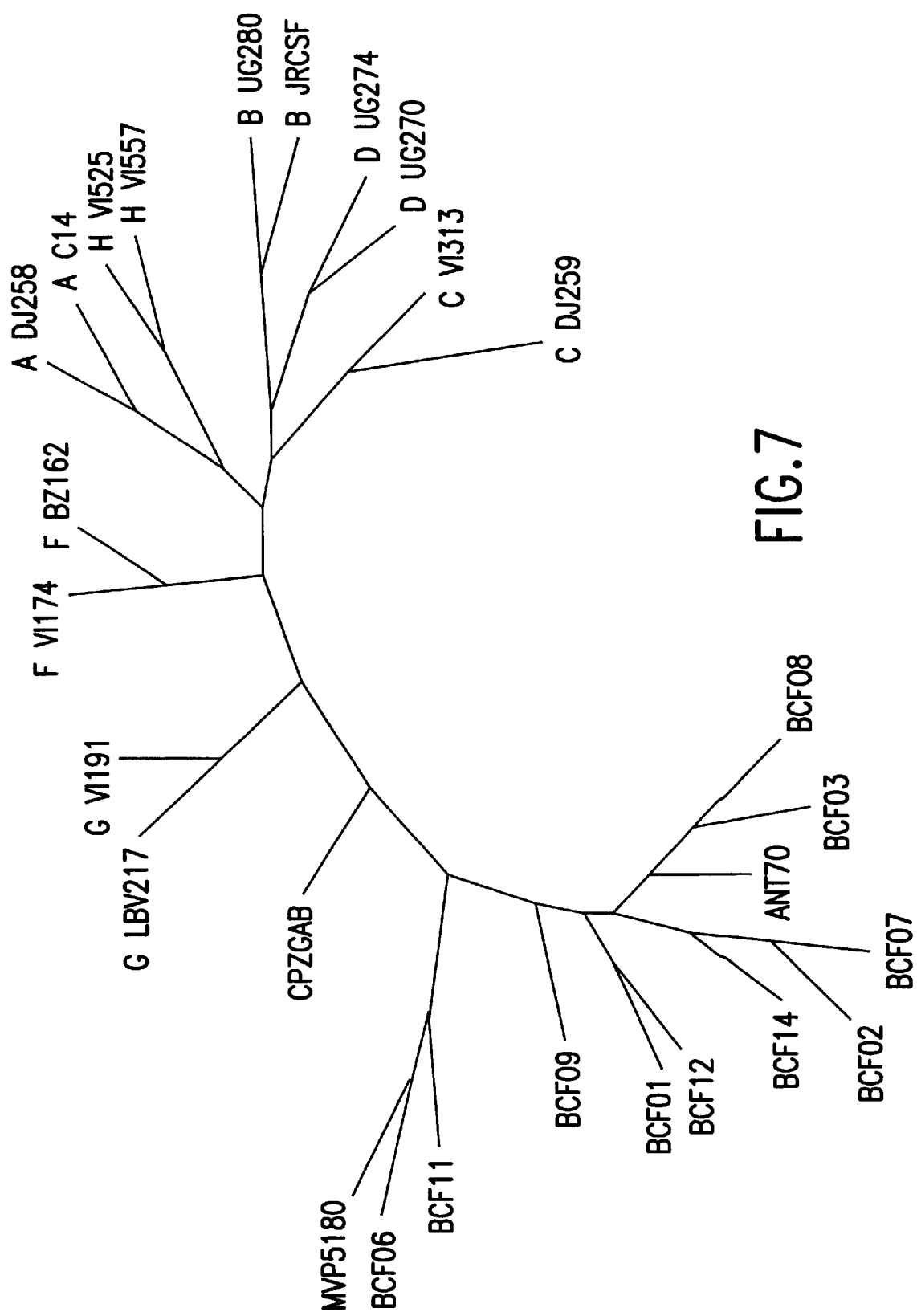
FIG. 7 illustrates a phylogenetic analysis based on the gag region.

FIGS. 6 and 7 correspond to a phylogenetic analysis based on the gag region.

The phylogeny of the gag genes confirms the dispersion of these variants and the difficulty in regrouping them either into subtype, or even into an exclusion group and shows the need for a selection of variants exhibiting particular phenetic and genetic characters and whose corresponding sera have characteristic reactivity and non-reactivity profiles capable of allowing the detection of HIV-1 in sera previously considered to be false-negative.

As evident from the above, the invention is not at all limited to its embodiment, implementation and application which have just been defined more explicitly; it embraces, on the contrary, all the variants which may occur to a specialist in this field, without departing from the framework or the scope of the present invention.

What is claimed is:

1. An isolated nucleic acid obtained from a group of O HIV-1, wherein the sequence of said nucleic acid is selected from the group consisting of:

SEQ ID NO:1, SEQ ID NO:2, SEQ ID NO:3, SEQ ID NO:4, SEQ D NO:5, SEQ ID NO:6, SEQ ID NO:7, SEQ ID NO:50, SEQ ID NO:51, SEQ ID NO:52, SEQ ID NO:53, SEQ ID NO:8, SEQ ID NO:9, SEQ ID NO:10, SEQ ID NO:11, SEQ ID NO:12, SEQ ID NO:13, SEQ ID NO: 14, SEQ ID NO:54, SEQ ID NO:55, SEQ ID NO:56, SEQ ID NO:57, SEQ ID NO:15, SEQ ID NO:16, SEQ ID NO:17, SEQ ID NO: 18, SEQ ID NO:19, SEQ ID NO:20, SEQ ID NO:21, SEQ ID NO:58, SEQ ID NO:59, SEQ ID NO:60, and SEQ ID NO:61.

2. A process for detecting a group of O HIV-1 comprising the steps:

extracting HIV-1 nucleic acid material from a biological sample containing said HIV-1 nucleic acid;

denaturing said HIV-1 nucleic acid;

annealing said denatured HIV-1 nucleic acid with at least one nucleic acid as claimed in claim 1 to form a hybrid;

extending the hybrid;

detecting the extended hybrid.

3. The process of claim 2, wherein said biological sample is obtained from serum or circulating lymphocytes.

4. The process of claim 2, wherein said step of extending the hybrid comprises addition of DNA polymerase and deoxyribonucleic acids.

5. The process of claim 2, wherein after said extracting the nucleic acid is treated with reverse transcriptase.

6. A process for screening and typing group O HIV-1, comprising bringing any of the nucleotide fragments in accordance with claim 1 into contact with the nucleic acid of the virus to be typed and detecting the hybrid formed.

7. An in vitro diagnostic reagent for a group of O HIV-1, comprising a sequence according to claim 1.

8. An in vitro diagnostic reagent for a group of O HIV-1, wherein said diagnostic reagent is selected from the group consisting of SEQ ID NOS: 22, 23, 24, and 25, which sequences may be used as primers for the amplification of a gp41 fragment from a group O HIV-1 viruses.

* * * * *